United States Patent
Bednarik et al.

(10) Patent No.: US 11,506,887 B2
(45) Date of Patent: Nov. 22, 2022

(54) METHOD AND APPARATUS FOR GAZE DETECTION

(71) Applicant: SeeTrue Technologies Oy, Joensuu (FI)

(72) Inventors: Roman Bednarik, Joensuu (FI); Piotr Bartczak, Joensuu (FI); David Gil De Gómez, Joensuu (FI)

(73) Assignee: SeeTrue Technologies Oy, Joensuu (FI)

(*) Notice: Subject to any disclaimer, the term of this patent is extended or adjusted under 35 U.S.C. 154(b) by 204 days.

(21) Appl. No.: 16/760,293

(22) PCT Filed: Oct. 30, 2018

(86) PCT No.: PCT/FI2018/050790
§ 371 (c)(1),
(2) Date: Apr. 29, 2020

(87) PCT Pub. No.: WO2019/086759
PCT Pub. Date: May 9, 2019

(65) Prior Publication Data
US 2020/0257113 A1 Aug. 13, 2020

(30) Foreign Application Priority Data
Oct. 30, 2017 (FI) .................................. 20175960

(51) Int. Cl.
*G02B 27/00* (2006.01)
*G06F 16/335* (2019.01)
(Continued)

(52) U.S. Cl.
CPC ......... *G02B 27/0093* (2013.01); *G06F 1/163* (2013.01); *G06F 3/013* (2013.01);
(Continued)

(58) Field of Classification Search
CPC . G02B 27/0093; G06F 16/337; G06F 16/436; G06F 16/437; G06F 16/163;
(Continued)

(56) References Cited

U.S. PATENT DOCUMENTS 6,005,710 A 12/1999 Pensel et al.
10,268,268 B1 * 4/2019 Trail .................. G06F 3/013
(Continued)

FOREIGN PATENT DOCUMENTS

CN 107002957 B 3/2021
EP 2499960 A1 9/2012
(Continued)

OTHER PUBLICATIONS

Finnish Patent and Registration Office, Office Action, Application No. 20175960, dated Feb. 26, 2020, 15 pages.
(Continued)

*Primary Examiner* — Yuzhen Shen
(74) *Attorney, Agent, or Firm* — Ziegler IP Law Group, LLC

(57) ABSTRACT

A method and apparatus for determining gaze direction information, includes a light source for forming illuminating light to an eye region of a user, and optical element(s) configured to guide the illuminating light from the light source to the eye region. The illuminating light is dynamically adjustable to generate a dynamic light beam on the eye region, and a sensor is configured to capture reflected light on the eye region and generate reflection eye data. The apparatus can maintain user profile information, adjust spectral power distribution of the light source based on the user profile information, receive the reflection eye data, and generate the gaze direction information based on the reflection eye data.

17 Claims, 5 Drawing Sheets

(51) Int. Cl.
*G06F 16/435* (2019.01)
*G06F 1/16* (2006.01)
*G06F 3/01* (2006.01)
*G06V 10/40* (2022.01)
*G06V 10/141* (2022.01)
*G06V 10/143* (2022.01)
*G06V 10/58* (2022.01)

(52) U.S. Cl.
CPC .......... *G06F 16/337* (2019.01); *G06F 16/436* (2019.01); *G06F 16/437* (2019.01); *G06V 10/141* (2022.01); *G06V 10/143* (2022.01); *G06V 10/40* (2022.01); *G06V 10/58* (2022.01)

(58) Field of Classification Search
CPC ........ G06F 3/013; G06K 9/2018; G06K 9/46; G06K 9/00597
See application file for complete search history.

(56) References Cited

U.S. PATENT DOCUMENTS

| | | |
|---|---|---|
| 2009/0030619 A1 | 1/2009 | Kameyama |
| 2011/0304820 A1 | 12/2011 | Falt et al. |
| 2013/0114043 A1 | 5/2013 | Balan et al. |
| 2014/0055747 A1 | 2/2014 | Nistico et al. |
| 2014/0184775 A1 | 7/2014 | Drake et al. |
| 2015/0061995 A1 | 3/2015 | Gustafsson et al. |
| 2015/0199006 A1 | 7/2015 | He et al. |
| 2015/0199559 A1 | 7/2015 | Sztuk et al. |
| 2015/0205259 A1 | 7/2015 | Kim et al. |
| 2016/0019421 A1 | 1/2016 | Feng et al. |
| 2016/0131902 A1 | 5/2016 | Ambrus et al. |
| 2016/0139265 A1 | 5/2016 | Yahav et al. |
| 2016/0232408 A1* | 8/2016 | Lee ................ A61B 5/7435 |
| 2016/0274659 A1 | 9/2016 | Caraffi et al. |
| 2017/0031435 A1 | 2/2017 | Raffle et al. |
| 2020/0278539 A1* | 9/2020 | Petljanski ............. G06F 3/0304 |

FOREIGN PATENT DOCUMENTS

| | | |
|---|---|---|
| EP | 3062142 A1 | 8/2016 |
| WO | 2016045911 A1 | 3/2016 |
| WO | 2016146486 A1 | 9/2016 |

OTHER PUBLICATIONS

Finnish Patent and Registration Office, Search Report, Application No. 20175960, dated May 21, 2018, 2 pages.
International Search Report, Application No. PCT/FI2018/050790, dated Mar. 28, 2019, 6 pages.
Written Opinion of the International Searching Authority, Application No. PCT/FI2018/050790, dated Mar. 28, 2019, 4 pages.
European Patent Office, Extended Search Report, Application No. 18872252.4, dated Jun. 30, 2021, 7 pages.
European Patent Office, Communication pursuant to Article 94(3) EPC, Application No. 18872252.4, dated Mar. 11, 2022, 6 pages.

* cited by examiner

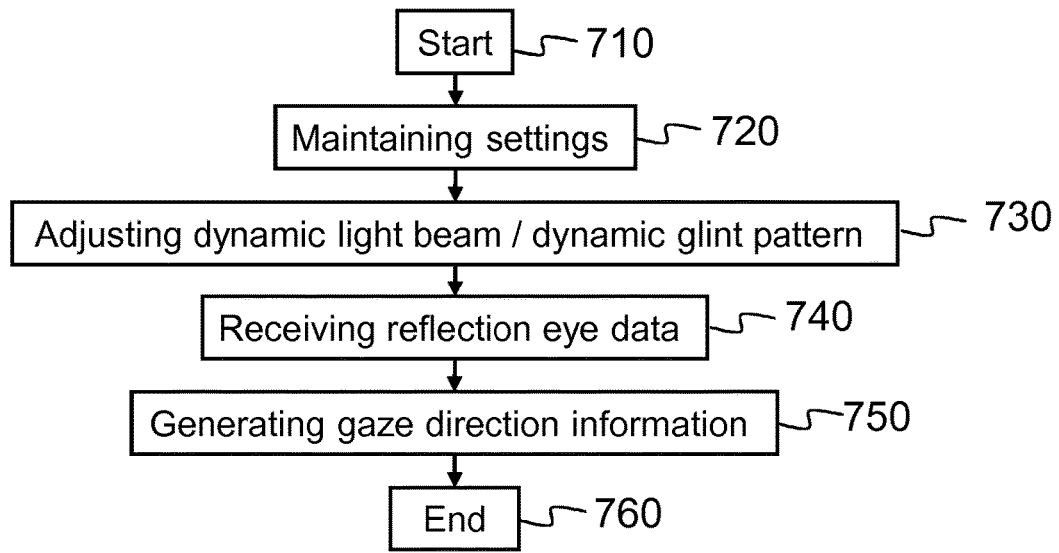
Fig. 7
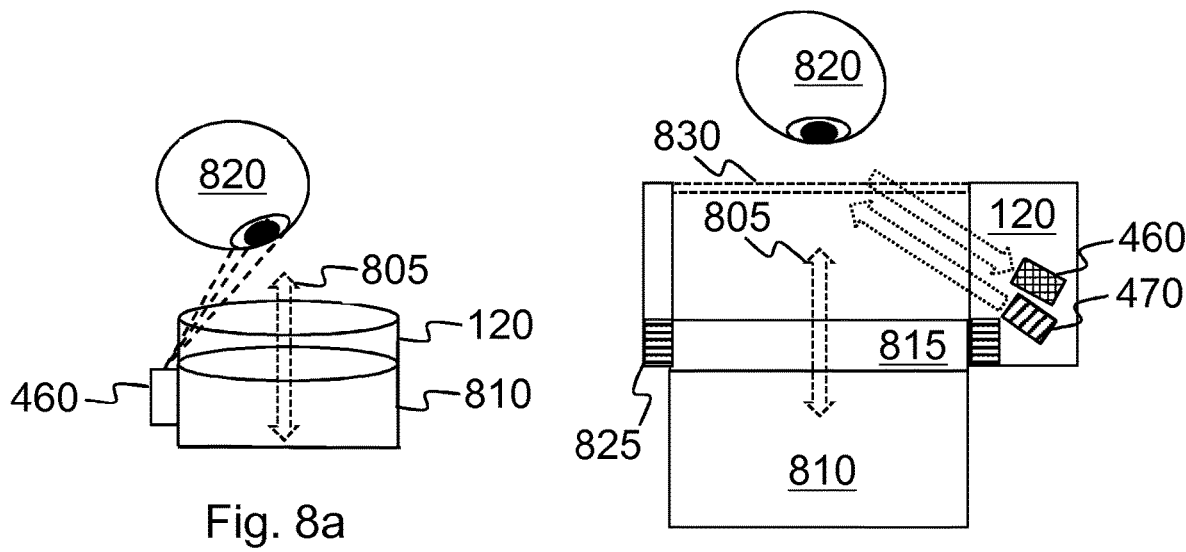
Fig. 8a
Fig. 8b
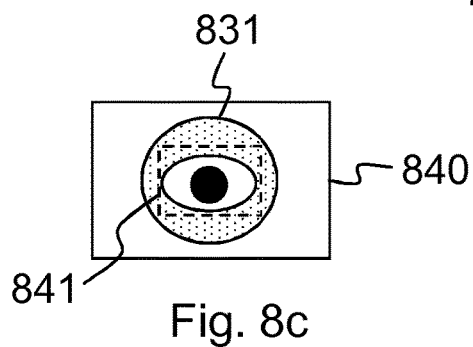
Fig. 8c

METHOD AND APPARATUS FOR GAZE DETECTION

TECHNICAL FIELD

The present application generally relates to eye-tracking and gaze detection. More particularly, but not necessarily, it relates to improving the robustness of eye-tracking.

BACKGROUND

This section illustrates useful background information without admission of any technique described herein representative of the state of the art.

A trend toward miniaturization of computing hardware, peripherals, as well as of sensors, detectors, and processors, among other technologies, has helped open up a field sometimes referred to as "wearable computing." As the data processing capabilities get more powerful, also more accurate human based control data is needed.

For example in microsurgery, the operative field is illuminated and magnified by an operating microscope. Student and resident in this field often learns and gets experience via watching video or by being present in the surgery. An operational microscope system that employs eye-tracking techniques in order to capture more accurately and more easily the position of gaze of a user viewing an object through the near-to-eye optical device, such as microscope eyepiece, would provide relevant advantage.

In wearable interactive displays, direction of gaze can be used to improve user experience through accurate prediction of objects of interest and to better utilize the limited computational resources, for example by focusing the computation on the gazed parts of the scene while omitting the not important ones.

Thus, a solution is needed to enable low-cost, accurate and efficient detection of gaze and determine gaze-direction based control data. Especially, a robust and power efficient solution would provide an advantage. Typically, known methods rely on image processing to highlight and track features on the eye surface, and suffer from large volumes of image data being processed. This creates a bottleneck, as the acquired eye-image data typically has to be processed pixel-wise for detection of regions important to feature separation. In particular, this requirement results in expensive processing units that consume high amounts of time and power. Consequently, eye-tracking systems are not robust to changes in the eye-region, may get bulky, slow, complex and heavy.

SUMMARY

An objective of certain embodiments of the present disclosure is to provide enhancement of captured image information/a rapid optical contrast enhancement between a number of selected features of an eye of a user. Certain disclosed methods and apparatus allow an optical real-time enhancement without additional image post processing and result in robust and low-cost, accurate and efficient detection of gaze.

Various aspects of examples of the disclosed embodiments are set out in the claims.

According to a first example aspect of the present disclosure, there is provided an apparatus for determining gaze direction information, comprising:

a light source for forming illuminating light to an eye region of a user;

optical element(s) configured to guide the illuminating light from the light source to the eye region, wherein the illuminating light is (or is configured to be) dynamically adjustable to generate a dynamic light beam (or beams) on the eye region;

a sensor configured to capture reflected light from the eye region and generate reflection eye data;

at least one processor and at least one memory including computer program code; the at least one memory and the computer program code being configured, with the at least one processor, to cause the apparatus to:

maintain settings comprising user profile information;

adjust spectral power distribution of the light source based on the user profile information;

receive the reflection eye data; and generate the gaze direction information based on the reflection eye data.

In an embodiment, the gaze direction information is determined based on a glint pattern or, as more closely defined, based on information from the surface of an eye (or based on information reflected/captured from the eye surface).

In an embodiment, the light source is configured to emit light in different spectral bands.

In an embodiment, the optical element(s) are freeform optical element(s).

In an embodiment, the optical element(s) or freeform optical element(s) are configured to guide and form the illuminating light from the light source to the eye region. The eye region in this context means one or more regions of an eye of the user.

In an embodiment, the optical element(s) or freeform optical element(s) are configured to collect and to intermix emitted components of the light. In an embodiment, the optical element(s)/freeform optical element(s) are configured to collect and to intermix all emitted components of the light.

In an embodiment, a spectral power distribution (SPD) of the formed or newly formed illuminating light or dynamic light beam is homogenized by means of optics (or the optical element(s) or freeform optical element(s)). The formed (dynamic) light beam/illuminating light illuminates the eye.

In an embodiment, spectral power distribution of the illuminating light is dynamically adjusted or adjustable to produce a dynamic light beam or beams. In an embodiment, the produced dynamic light beam illuminates the eye region(s) so as to generate glint(s) on the eye region(s). In an embodiment, spectral power distribution of the illuminating light is dynamically adjusted or adjustable to produce a dynamic light beam to enhance contrast/captured image information between selected features of the eye. In an embodiment, the illuminating light is dynamically adjusted or adjustable to produce a dynamic light beam to enhance captured image information e.g., contrast between selected features of the eye, and concomitantly to generate a glint on the eye region.

In an embodiment, the illuminating light is dynamically adjusted or adjustable to produce a dynamic glint pattern on the eye region.

In an embodiment, illuminating light is directly pointed to pre-selected regions of the eye. In an embodiment, the dynamic light beam is mixed and guided into pre-selected regions, e.g., by optical fibers. In an embodiment, a mixture of light directed to different regions is dynamically selected.

In an embodiment, the apparatus comprises a light source capable of emitting light in different wavelengths (of the electromagnetic spectrum). In an embodiment, the apparatus comprises a light source capable of emitting light in different wavelengths to form designed light illuminating one or more regions or the (whole) eye of a user.

In an embodiment, the apparatus comprises the optics (optical element(s)) to collect and intermix spectral components or all spectral components of the illuminating light, and then to guide the illuminating light in accordance with newly formed SPD to the eye region(s).

In an embodiment, the sensor is configured to capture reflected glint pattern of the eye region(s) and generate reflection eye data. In an embodiment, the sensor is configured to capture a dynamic light beam reflected from the eye region(s) and generate reflection eye data. In an embodiment, the sensor is configured to capture a reflected dynamic light beam illuminating the eye and concomitantly generated glint(s) on the eye region(s) and generate reflection eye data.

In an embodiment, the apparatus comprises a communication interface for transceiving information. In an embodiment, the communication interface is an internal interface or a device internal interface. In an embodiment, the communication interface is an interface for transceiving information over a network. In an embodiment, the network is a wireless network. In an embodiment, the network is a short-range network. In an embodiment, the network is a cellular network. In an embodiment, the network is a telecom operator's network.

In an embodiment, the optical element(s), such as an optical lens, optical fibers, waveguide, and homogenizing rod, is/are configured to collect and to intermix emitted components/all emitted components of the light source what consequently generates homogenous dynamic light beams illuminating the eye or the eye's region.

In an embodiment, the user profile information comprises information on optical properties of a user's eye. In an embodiment, the user profile information comprises latest updated SPD settings concerning the user. In an embodiment, the user profile information comprises latest updated SPD settings to maximize contrast between selected features of the user's eye. In an embodiment, the user profile information comprises light calibration data. In an embodiment, the user profile data comprises optical properties of a user's eye and latest updated SPD settings concerning the user. In an embodiment, the user profile information comprises one or two or all of the following: optical properties of a user's eye, latest updated SPD settings concerning the user, and light calibration data. In an embodiment, the settings further comprise environmental information of the apparatus. In an embodiment, the apparatus is caused to adjust spectral power distribution of the light source based on both the user profile information and environmental information of the apparatus.

In an embodiment, the user profile information comprises eye optical properties and the at least one memory and the computer program code are configured to, with the at least one processor, cause the apparatus to:
adjust the spectral power distribution of the light source based on the eye optical properties.

In an embodiment, the apparatus comprises the optical element(s) to collect and to intermix emitted components of the light source to generate dynamic light beam(s) illuminating the eye region.

In an embodiment, the apparatus is caused to adjust the dynamic light beam or dynamic glint pattern by adjusting spectral power distribution of the light source based on the user profile information.

According to a further example apparatus aspect of the present invention, there is provided an apparatus for determining gaze direction information based on a glint pattern, comprising:
a light source for forming illuminating light to an eye region of a user;
freeform optical elements configured to guide and form the illuminating light from the light source to the eye region, wherein the illuminating light is configured to be dynamically adjustable to generate a dynamic glint pattern on the eye region;
a sensor configured to capture reflected glint pattern of the eye region and generate reflection eye data;
a communication interface for transceiving information over a network;
at least one memory including computer program code;
the at least one memory and the computer program code configured to, with the at least one processor, cause the apparatus to:
maintain settings comprising at least one of the following:
environmental information of the apparatus; and
user profile information;
adjust the dynamic glint pattern based on the settings;
receive the reflection eye data; and
generate the gaze direction information based on the reflection eye data.

In an embodiment, the dynamic glint pattern is adjusted by adjusting spectral power distribution of the light source. In a further embodiment, the dynamic glint pattern may additionally be adjusted by adjusting spatial properties of the illuminating light. In an embodiment, spatial properties of newly formed illumination with designed SPD are adjusted by, e.g., activating or deactivating separate transmitters in case the light source has a plurality of transmitters.

In an embodiment, the light source comprises a plurality of light transmitters, at least one of them being configured to emit light in different spectral band and in different or the same intensity.

In an embodiment, the at least one memory and the computer program code configured to, with the at least one processor, cause the apparatus to:
adjust spectral power distribution of at least one light transmitter, such as infrared Light Emitting Diode (LED), based on the settings.

In an embodiment, at least one of the light transmitters, such as infrared Light Emitting Diode (LED), is configured to emit light with wavelength between 1000-2600 nm. In other embodiments, at least one of the light transmitters, such as infrared Light Emitting Diode (LED), is configured to emit light with wavelength between 900-2600 nm. Intensity of each transmitter can be configured separately.

In an embodiment, the optical element(s) is configured to collect and to intermix emitted components of the light source, which consequently generates dynamic light beams illuminating the eye or the eye region. In an embodiment, the optical elements comprise at least one of the following: an optical lens, optical fibers, waveguide, and homogenizing rod.

In an embodiment, the freeform optical elements comprise at least one of the following: an optical lens and optical fibers, configured to generate the dynamic glint pattern on the eye region.

In an embodiment, the apparatus is exchangeably attached as an input device to a second apparatus.

In an embodiment, the second apparatus is a see-through optical device or a close-to-eye optical device, such as a microscope, binoculars, an AR (augmented reality) device or a VR (virtual reality) device, or a MR (mixed reality) device.

In an embodiment, the apparatus is attached adjacent to an ocular of the second optical apparatus, such as a microscope, so that visible light coming through the ocular or other see-through optical device is transmitted to the eye without being disturbed by the apparatus.

In an embodiment, the apparatus further comprises a reference element configured to reflect back light emitted from the light source to provide reflected reference data to the sensor, wherein the reference element is arranged so that the visible light coming through the ocular or the see-through optical device is transmitted to the eye without being disturbed by the reference element.

In an embodiment, the at least one memory and the computer program code are configured to, with the at least one processor, cause the apparatus to:
conduct spectral calibration of the apparatus by performing at least the following steps:
scan the eye of the user through different spectral bands, or combinations of spectral bands, of the light source and capture an image by the sensor for each different spectral band;
compare image attribute(s) of at least two captured images;
select at least one image based on the comparison;
define an attribute value and/or create an index list based on the significance of the selected image;
determine intensity of at least one spectral band using the attribute value and/or index list; and
adjust the settings based on the conducted spectral calibration.

Examples of image attributes are contrast, brightness, luminance level, and other quantities of the feature regions contingent on the illumination distribution. Examples for defining contrast values, e.g. for a contrast index, are Michelson, Weber, and Root mean square contrast.

In an embodiment, the at least one memory and the computer program code are configured to, with the at least one processor, cause the apparatus to:
calibrate the apparatus by performing at least following steps:
scan the eye of the user through different spectral bands of the light source and capture an image by the sensor for each different spectral band;
compare contrast information of at least two captured images;
select at least one image based on the comparison;
define contrast index based on the selected image;
determine intensity of at least one spectral band using the contrast index; and
adjust the settings based on the calibration step.

In an embodiment, the sensor comprises a video camera adapted to detect light and configured to detect the reflected glint pattern of the eye.

In an embodiment, the at least one memory and the computer program code are configured to, with the at least one processor, cause the apparatus to:
receive settings, from a cloud server, comprising at least one of the following:
user profile information containing optical properties of user's eye and/or latest updated SPD settings to maximize contrast between selected features, and/or data from spectral calibration; and
environmental information of the apparatus; and
adjust the illuminating light based on the settings.

In an embodiment, the at least one memory and the computer program code are configured to, with the at least one processor, cause the apparatus to:
receive settings, from a cloud server, comprising at least one of the following:
environmental information of the apparatus; and
user profile information; and
adjust the dynamic glint pattern based on the settings.

In an embodiment, the at least one memory and the computer program code are configured to, with the at least one processor, cause the apparatus to:
transmit the gaze direction information to a second apparatus as input data.

In an embodiment, the apparatus comprises a user wearable apparatus.

In an embodiment, the at least one memory and the computer program code are configured to, with the at least one processor, cause the apparatus to:
capture eye's optical characteristics data of a user;
transmit the eye's optical characteristics data to a cloud server for identification;
receive settings from a cloud server, comprising user profile information in response to determining identification by the cloud server; and
adjust the illuminating light based on the settings.

In an embodiment, the at least one memory and the computer program code are configured to, with the at least one processor, cause the apparatus to:
capture eye characteristic data of a user;
transmit the eye characteristic data to a cloud server for identification;
receive settings from a cloud server, comprising user profile information in response to determining identification by the cloud server; and
adjust the dynamic glint pattern based on the settings.

In an embodiment, the at least one memory and the computer program code configured to, with the at least one processor, cause the apparatus to:
capture eye's optical characteristics data of a user;
adjust the illuminating light to produce a dynamic light beam;
update the user profile information based on the dynamic light beam associated with the eye's optical characteristics data;
determine environmental information of the apparatus;
transmit updated settings to a cloud server, comprising at least one of the following:
user profile information containing optical properties of user's eye and/or latest updated SPD settings to maximize contrast between selected features, and/or data from spectral calibration; and
environmental information of the apparatus.

In an embodiment, the at least one memory and the computer program code are configured to, with the at least one processor, cause the apparatus to:
capture eye characteristic data of a user;
adjust the dynamic glint pattern;
update the user profile information based on the dynamic glint pattern associated with the eye characteristic data;
determine environmental information of the apparatus;
transmit updated settings to a cloud server, comprising at least one of the following:
environmental information of the apparatus; and
updated user profile information.

In an embodiment, the apparatus of the first aspect is an imaging device.

According to a further example aspect of the present disclosure, there is provided an imaging device for determining gaze direction information based on a glint pattern, comprising:

a light source for forming light to an eye region of a user;

freeform optical elements configured to guide and form the light from the light source to the eye region, wherein the light is configured to be dynamically adjustable to generate a dynamic glint pattern on the eye region;

a gaze detection component configured to capture an image of the eye region;

a communication interface for transceiving information with an apparatus, the apparatus comprising a sensor configured to determine reflected glint pattern of the eye region based on the image of the eye region and generate reflection eye data, maintain settings comprising at least one of the following: environmental information of the apparatus; and user profile information; adjust the dynamic glint pattern based on the settings; receive the reflection eye data; and generate the gaze direction information based on the reflection eye data.

In an embodiment, an imaging light guide between a user eye and a sensor comprise a borescope tube.

According to a second example aspect of the present disclosure, there is provided a method for determining gaze direction information in an apparatus comprising a light source for forming illuminating light to an eye region of a user, optical element(s) configured to guide the illuminating light from the light source to the eye region, wherein the illuminating light is (or is configured to be) dynamically adjustable to generate a dynamic light beam (or beams) on the eye region, and a sensor configured to capture reflected light from the eye region and generate reflection eye data, the method comprising:

maintaining settings comprising user profile information;

adjusting spectral power distribution of the light source based on the user profile information;

receiving the reflection eye data; and generating the gaze direction information based on the reflection eye data.

In an embodiment, the method comprises collecting and intermixing emitted components of the light source to generate dynamic light beam(s) illuminating the eye region.

In an embodiment, the illuminating light is dynamically adjustable to generate a glint or a dynamic glint pattern on the eye region.

According to a further example method aspect of the present disclosure, there is provided a computer implemented method for determining gaze direction information based on a glint pattern, comprising:

maintaining settings comprising at least one of the following:

environmental information of an apparatus; and user profile information;

adjusting a dynamic glint pattern based on the settings, wherein freeform optical elements are configured to guide and form illuminating light from a light source to eye region, and the illuminating light is configured to be dynamically adjustable to generate the dynamic glint pattern on the eye region;

receiving reflection eye data from a sensor configured to capture reflected glint pattern of the eye region and generate the reflection eye data; and generating the gaze direction information based on the reflection eye data.

Different non-binding example aspects and embodiments of the present disclosure have been illustrated in the foregoing. The embodiments in the foregoing are used merely to explain selected aspects or steps that may be utilized in implementations of the present disclosure. Some embodiments may be presented only with reference to certain example aspects of the present disclosure. It should be appreciated that corresponding embodiments may apply to other example aspects as well.

BRIEF DESCRIPTION OF THE DRAWINGS

For a more complete understanding of example embodiments of the present disclosure, reference is now made to the following descriptions taken in connection with the accompanying drawings in which:

FIG. 7 shows a flow chart of a process of an example embodiment;

FIGS. 8a-c show schematic drawings of a gaze detector used for generating a dynamic glint pattern/dynamic light beam in example embodiments.

DETAILED DESCRIPTION OF THE DRAWINGS

An example embodiment of the present disclosure and its potential advantages are understood by referring to FIGS. 1 through 7 of the drawings. In this document, like reference signs denote like parts or steps. In the following description, illuminating light in some embodiments refer to defined and produced light beam(s) from a light source. Adjusting/designing the illuminating light relates to adjusting (especially) spectral power distribution/spectral properties of the light beam. Dynamic light beam(s) are the light that illuminates the eye. The term "dynamic" is used to explain that spectral power distribution (SPD) of the dynamic light beam might be constantly adapting to the user's eye and/or selected eye features, and/or environmental changes. The adjusted/designed illuminating light/dynamic light beam is unique for each user. In an embodiment, the designed illuminating light/dynamic light beam is unique for each feature of the user's eye. Furthermore, a glint pattern refers to glint(s) on the eye surface, and adjusting the glint pattern relates to changing the glint pattern. The changing of the glint pattern refers to spectral changes in the glint(s) rather than to spatial changes in the illuminating light. However, in some embodiments, spatial changes may also be performed in addition to the spectral changes. Furthermore, generating a dynamic glint pattern in many occasions refers to generating a dynamic light beam that illuminates the eye region(s). In an embodiment, illuminating light beam(s) are inseparably connected with the glints, generating a dynamic glint pattern. A beam in some embodiments refers to a bundle of light or a bundle of single beams. Each bundle of light might have the same or different SPD. Each bundle of light produces concomitantly glint(s) on the eye. In an embodiment, dynamic glints are enhancing captured image information between (and/or for) selected features of the eye.

Figure 1:
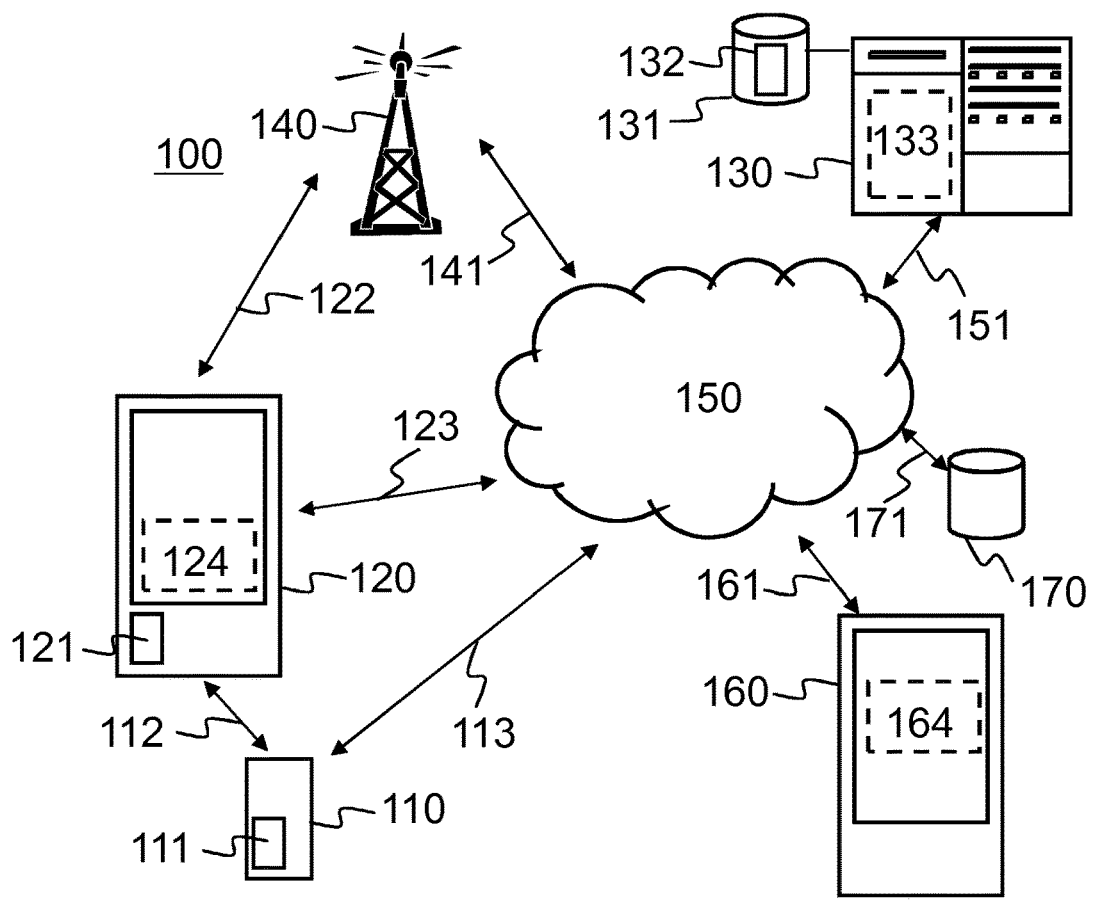
FIG. 1 shows a schematic drawing of a system of an example embodiment.

FIG. 1 shows a schematic picture of a system 100 according to an example embodiment of the present disclosure.

The system comprises a client device 120 that may comprise a multimedia device, a mobile phone, an Internet tablet or a laptop computer, for example. The client device 120 is capable of downloading and locally executing software program code. The software program code may be a proprietary client application 124 of a service whose server application 133 is running on the server apparatus 130 of the system 100. The client device 120 may comprise a metadata element 121 for creating data usable as metadata relating to control input of the proprietary application 124, such as eye-tracking application or application using eye-tracking information as input data.

The metadata element 121 may comprise at least one of the following: a microphone, an eye-tracker, a sensor, a gaze detection apparatus, a positioning device for determining the current location of the apparatus 120, and a local clock. The client device 120 is configured to be connectable to a wireless communication network 140 over a wireless connection 122. The wireless connection 122 may comprise a mobile cellular network or a wireless local area network (WLAN), for example. The wireless communication network 140 may be connected to a public data communication network 150, for example to the Internet, over a data connection 141. The proprietary application 124 may be operable also in offline mode and there is no need to have online connection over the network to the server 130, 131 all the time. In offline mode, the client device 120 may store application related data to cache memory and update the data to the server 130, 131 once getting the online access or at least one of the subject user, the proprietary application or the server application triggers or requests to synchronize or upload data, for example.

In an embodiment, the system 100 comprises a personal device 110 configured to be capable of capturing gaze detection related data. The personal device 110 may comprise storage 111 for the gaze detection related data. The storage 111 may comprise a flash memory card, for example. The personal device 110 is configured to be connectable to the client device 120 over a data connection 112. The data connection 112 may be a wired connection or a wireless connection. The wired connection may comprise Universal Serial Bus (USB), High-Definition Multimedia Interface (HDMI) or local area network (LAN), for example. The wireless connection may comprise Bluetooth™, Radio Frequency Identification (RF-ID) or wireless local area network (WLAN), for example.

The personal device 110 is configured to send captured data over the data connection 112 to the client device 120. Such transmittal may be initiated by a user of the personal device 110, by a user of the client device 120, or automatically based on settings. Such settings may comprise for example time of the day, amount of newly captured gaze detection related data or existence of the data connection 112 for the personal device 110.

In an embodiment, the proprietary application 124 may comprise a plurality of client applications. A first client application may comprise a gaze detection application according to embodiments disclosed. A second client application may comprise a dynamic glint pattern adjustment application (or a dynamic light beam adjustment application).

In an embodiment, the system 100 comprises a server apparatus 130, which comprises a storage device 131 for storing gaze detection related information, such as dynamic glint pattern data (or dynamic light beam data), settings, user profile information, environmental information of the apparatus 110, 120, event logs and metadata received over a data connection 151, user profile information of users, credentials, history information of users, client software application data and server software application data, for example. In an embodiment, the user profile information contains optical properties of user's eye and/or latest updated spectral power distribution (SPD) settings to maximize contrast between selected features, area and type of selected features, and/or data from spectral calibration.

In an embodiment, the system 100 may further comprise other user apparatuses 160, connected to the network 150 over connection 161, wherein tasks relating to the service system may be processed. The user apparatus 160 may comprise a peer apparatus for augmented reality (AR) related application with the user apparatus 120, for example.

Different apparatuses 110, 120, 130, 160, 170 may provide gaze detection related information to be maintained in the service system 100. The information may be maintained as a collaborative record 132 within the server apparatus 130, 131. The collaborative record 132 may comprise any gaze detection related information provided by different users, the service system or sensors, for example.

Furthermore, the coordinator of an apparatus 160 may administer settings, gaze direction information and user data. The system service 130, 131 and its server application 133 may receive user or gaze detection related data generated by the proprietary application 124 of the client device 120 as input and process the received data.

In an embodiment, a server apparatus 130 maintains the service system data, such as gaze detection related records. Each record may be identified using a unique identifier. Furthermore, a subject user identifier may be used to identify each subject user. The subject user identifier may comprise, for example a unique number, iris detection information, string or an e-mail address, for example. In general, user identifier must be unique but not something based on which someone can recognize or identify the user. In an embodiment, a unique SPD of the dynamic light beam is used for identifying the subject.

Information relating to gaze detection related data may be transmitted to the server 130 from a plurality of apparatuses 110, 120, 160 over the network 150. Eventually, the received service data is maintained, by an operator, at the server 130 comprising storage device 131, wherein the data being available for users having access to that particular record. Furthermore, metadata associated with the service data may also be stored in the server 130 or storage device 131, such as iris detection data, glint pattern data, location information, time information, or a device identifier, for example. In an embodiment, data on the SPD of the dynamic light beam and position of concomitantly generated glint(s) on the eye region is used.

In an embodiment, gaze detection related data may be transferred to a server apparatus 130 over different paths. A first path may comprise sending data captured by a proprietary application (e.g. a gaze detection client application) of a client device 120 over a wireless communication network 122, 140, 141 and public data communication network 150, 151 to the server apparatus 130. A second path may comprise sending data captured by a default application of a client device 120 over a wireless communication network 122, 140, 141 and public data communication network 150, 151 to the server apparatus 130. A third path may comprise sending data captured by a personal device 110 (such as user wearable sensor or imaging device) to the client device 120 over connection 112 and therefrom over a wireless communication network 122, 140, 141 and public data communication network 150, 151 to the server apparatus 130. A fourth path may comprise sending data captured by the device 110 to a computer apparatus 120 and therefrom over the connection 123 and the public data communication network 150, 151 to the server apparatus 130.

In an embodiment, the proprietary application in the client device 120 may be a client application of a service whose server application is running on the server apparatus 130 of the system 100. The proprietary application may capture the data for the first path. Also metadata for the captured multimedia may be retrieved by the proprietary application from the metadata elements 121 of the client device 120. For the second path, the data captured by the default application may be imported to the proprietary application before transmitting to the server apparatus 130. The proprietary application may check the data and extract and apply metadata for the data. For the third path, the data may be captured by the external device 110 and transmitted to the proprietary application of the client device 120 for sending to the server apparatus 130. The proprietary application may check the data and extract and apply metadata for the multimedia data. A user may provide additional metadata using the client device 120. For the fourth path, the data may be captured by the external device 110 and transmitted to a communication application of a computer apparatus 120.

In an embodiment, a proprietary or client application 164 in the user apparatus 160 (e.g. administrator apparatus) may be a peer or an administrator application of a service whose server application is running on the server apparatus 130 of the system 100.

In an embodiment, the personal device 110 may comprise a user wearable device communicating with the apparatus 120 over a local connection 112. The local connection 112 may comprise, for example, at least one of the Bluetooth, Radio Frequency Identification (RF-ID), near field communication (NFC) or other wireless non-cellular connection. The wireless non-cellular connection may comprise industrial, scientific and medical (ISM) radio bands that are radio bands (portions of the radio spectrum) reserved internationally for the use of radio frequency (RF) energy for industrial, scientific and medical purposes, for example. The local connection 112 may also comprise non-RF connection, such as Light Fidelity (Li-Fi), for example. Alternatively, the user wearable device 110 may be comprised by the apparatus 120, as illustrated by an integrated apparatus 120-121. The user wearable device 110 may also comprise a wearable garment. The apparatus 110, 120 may be for example a wrist or a head wearable user apparatus.

In an embodiment, the personal device 110, such as a user wearable device, may be paired with the client device 120. Pairing may be based on device identifiers of the devices 110, 120 and pairing information may be maintained within the subject user profile associated with the subject.

Furthermore, the personal device 110 may be connected to the network 150 over local connection 113 corresponding to connection 123, for example.

In an embodiment, a communication interface module of the device 120 may comprise location modules for tracking location of the portable apparatus 120. Such location modules may comprise a module for providing a connection to satellite based global positioning system (e.g. GPS, not shown), a module for cellular based positioning system, a module for wireless non-cellular positioning system (e.g. Wi-Fi) or a module for hybrid positioning system, for example. The positioning system may also be used for user speed detection, altitude detection, route detection and route planning for various embodiments.

In an embodiment, the client device 120 may be connected over a wireless or wired connection to a wide area network 150, such as Internet. Router apparatuses (not shown) may be used for providing the access to a wide area network 150. The access may comprise cellular or non-cellular connection.

In an embodiment, a proprietary application 124, such as a gaze detection application, in the device 120 may be a client application of a service whose server application is running on the server apparatus 130 of the system 100. The proprietary application 124 may capture the user input data for the service and provide the user output data from the service.

In an embodiment, at least parts of the apparatus 120 and/or the device 110 may be implemented as a chipset that comprises required communication interface, memory, program code and processor to perform the control algorithms for the dynamic glint pattern adjusting (e.g. determining optimal spectral power distribution, determining optimal glint pattern, controlling spectral power distribution and pattern generation/formation). In an embodiment, at least parts of the apparatus 120 and/or the device 110 may be implemented as a chipset that comprises a communication interface, memory, program code and processor to perform the control algorithms for the dynamic light beam adjustment (e.g. determining unique optimal spectral power distribution, determining optimal glint pattern, controlling generation/formation/mode of both spectral power distribution and concomitantly appearing glint(s)).

The server 130 may also provide a cloud service for the portable device 120 data. Optionally, further apparatuses may be added, such as peripheral devices for maintaining, providing or processing the portable device 120 data and communication devices for connecting the peripheral devices to the system 100.

In an embodiment, the system 100 may further comprise an external database 170. The external database 170 may be accessible to the network 150 over connection 171. The database 170 may have corresponding structure as the server apparatus 130, 131, for example.

Figure 2:
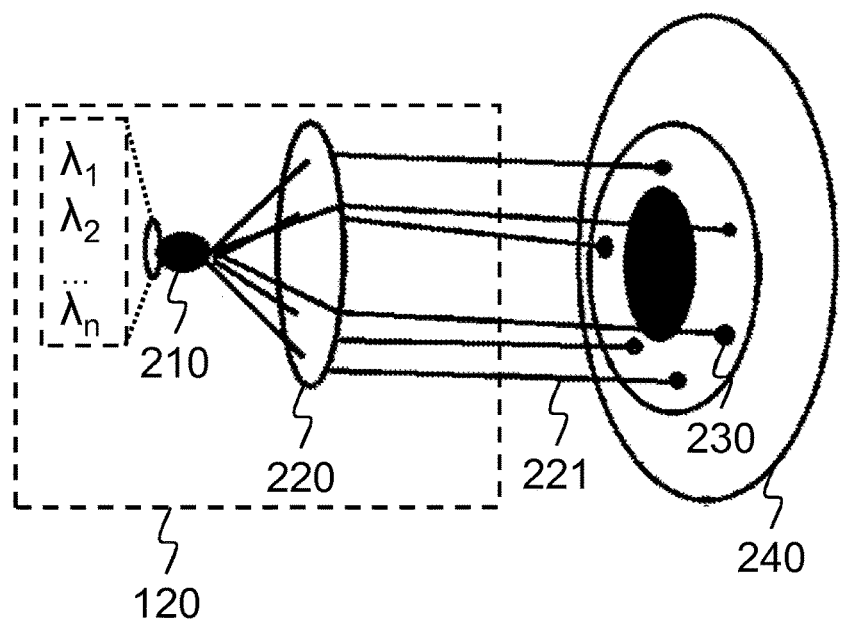
FIG. 2 shows a schematic drawing of generating a dynamic glint pattern/dynamic light beam in an example embodiment.

FIG. 2 shows a schematic drawing of a generating dynamic glint pattern or dynamic light beam(s) to enhance captured image information, e.g., contrast between selected features of the eye and concomitantly to generate glint(s) on the eye region in an example embodiment.

An apparatus 120 is configured to determine gaze direction information based on a glint pattern/based on information from the surface of an eye (or based on information reflected/captured from the eye surface). The apparatus 120 comprises a light source 210 for forming illuminating light to an eye region 240 of a user. The apparatus 120 comprises the light source 210 for forming designed SPD of the light illuminating an eye, wherein SPD of the illuminating light can be dynamically adjustable to produce a dynamic light beam to enhance contrast between selected features of an eye 240 of a user. Optical elements 220, such as freeform optical elements, are configured to guide and form the illuminating light 221 from the light source 210 to the eye region 240, wherein the illuminating light 221 is configured to be dynamically adjustable to generate a dynamic glint pattern 230 on the eye region 240. In an embodiment, the optical element(s) 220 are configured to collect and to intermix all emitted components of the light ($\lambda_1, \lambda_2, \ldots \lambda_n$). The SPD of newly formed light beam(s) 221 from the light source 210 is being homogenized by means of optics 220 and illuminates uniformly the entire eye 240 and concomitantly generates glint(s) 230 on the eye region, wherein the illuminating light 221 is configured to be dynamically adjustable both spectrally and optionally also spatially to generate an unique dynamic light beam and position of concomitantly generated glint(s) 230 on the eye region 240 of the user in question.

In an embodiment, dynamic adjusting of the illuminating light 221 may be performed using spectral power distribution of the light source 210. Intensity of the light source 210 can be manipulated and spectral power distribution can be changed by electric current/voltage levels that are obtained for an eye profile based on settings. The settings may be determined in a setup phase based on eye scanning and eye profile detection. The spectral power distribution of the light source may be controlled based on current/voltage/modulation (PWM). Alternative constant control modes may comprise, for example, constant voltage (CV), and constant current (CC). The spectral power distribution of the light source 210 may also be obtained by using spatial light modulator (SLM) devices with a combination of a dispersive element. Examples of the type of suitable SLM devices that could be employed are: Digital Micromirror Device (DMD) at the heart of DLP displays or LCoS Displays (Liquid crystal on silicon).

In embodiment, PWM mode may be used for improving eye safety. For example, power of the light source may be increased but shorter signals being made so that the total exposure of the eye is still within safety limits. PWM may also be applied to decrease energy consumption.

In an embodiment, characteristic data of the dynamic glint pattern (e.g. intensity, spectral power distribution, pattern formation) may be adjusted based on the settings. The settings may comprise at least one of the following: environmental information of the apparatus; and user profile information.

In an embodiment, optical properties of the dynamic light beam (e.g. intensity, spectral power distribution, activation mode and formed pattern) are adjusted based on the settings. The settings may comprise at least one of the following: user profile information, and environmental information of the apparatus.

The user profile information may comprise, for example, eye's optical properties and transmitter's optimized power distribution data. The user profile may comprise transmitter's optimized power distribution settings to maximize contrast between selected features. The user profile information may also comprise spectral properties of the imaging sensor after adaptation for detecting the light in specific range (infrared or the range above the visible range of the user, for example).

In an embodiment, the light source 210 may comprise several spectral bands that can be turned ON or OFF with different intensities and combinations. Such combination is generated by an algorithm based on input data (eye characteristics data such as spectral optical properties, eye colour, and detected distance of the eye from the imaging sensor, for example. Detected distance can be used for adjusting pattern (its distribution), light intensity, or focusing camera, for example. Thus, an adjustable (dynamic) glint pattern is obtained. In an embodiment, the light source 210 may comprise several spectral bands that can be turned ON or OFF with different intensities and combinations. Such combination is generated by an algorithm based on input data, including eye optical characteristics data such as spectral optical properties, eye colour, thickness and pigmentation of the sclera, chemical and anatomical composition of each region such as vascular structures, and detected distance of the eye from the imaging sensor, for example. Detected distance can be used for e.g., adjusting pattern (its distribution), light intensity, or focusing camera. Selected regions of the eye are composed of different biological tissue types. Based on their unique structure each eye region and layer of the surface have different optical properties (e.g., reflectance). Thus, interaction with illuminating light at various wavelengths of the electromagnetic spectrum can be specified and optimized. The unique amount of reflected/absorbed/transmitted light differs and can be characterized by the solution of spectral calibration and apparatus presented herein. Thus, an adjustable SPD of dynamic light beam and the position of concomitantly generated glint(s) on the eye region are obtained.

In an embodiment, the dynamic spectral power distribution may be adjusted so that the light source (one or several transmitters) being capable to provide several spectral bands that may be used for gaze detection to produce optimized spectral distribution to enhance system performance.

Optimized spectral power distribution is generated by selecting an optimal number of spectral bands at optimal intensity. In an embodiment, adjustable illumination together with freeform optical elements enables generating of dynamic optimized glint patterns. In an embodiment, adjustable illumination together with optical element(s) enables to collect and to intermix all emitted spectral components of the light source what consequently generates homogenous dynamic light beam illuminating the eye together with concomitantly generated glint(s) on the eye region.

The (freeform) optics 220 is configured to guide and form illumination of the eye region 240. In an embodiment, the optics 220 is configured to collect and to intermix all emitted spectral components of the light source and to form homogeneous illumination of the eye region 240. Both spectral and spatial properties of concomitantly formed shape of the glint(s) 230 can be adjusted and made unique. One source of illumination 210 may be used and the light 221 is collected, intermixed, shaped and divided using the optical elements 220. Thus the radiation reaching the eye 240 is easily controlled and kept within standard limits. The unique optimized glint pattern 230/dynamic light beam 221 illuminating the eye together with concomitantly generated glint(s) 230 simplifies and enhances eye-tracking algorithm and make the solution more robust and consume less energy. Intensity, spectral power distribution and position of a glint 230 may be dynamically adjusted by a control algorithm based on settings, even automatically without user interaction.

Furthermore, an adaptive lighting 221 of the light source 210 may be provided to create optimal spectral illumination and power for illumination. The adaptivity takes into account optical properties of each individual's eye regions 240 and surrounding light conditions. The illumination by the light source 210 can be adapted to each user in order to provide the best final system performance. Settings are stored and can be loaded anytime. The illumination is also optimized with sensitivity of an imaging sensor (not shown) used. The SPD of illumination may also be optimized with sensitivity of the sensor after adaptation. That is different since it includes information about the cut-off filter, for example.

The illustrated apparatus 120 fits well for wearable non-tethered devices where energy consumption is important and surrounding incident light conditions are changing.

In an embodiment, the light source 210 may comprise a plurality of light transmitters, at least one of them being configured to emit light in different spectral bands (as illustrated by different wavelengths $\lambda_1$-$\lambda_n$), and spectral power distribution of at least one transmitter may be adjusted based on the settings. At least one of the light transmitters may be configured to emit light with wavelength between 1000-2600 nm or between 900-2600 nm in some embodiments.

Intensity of each transmitter can be configured separately.

A light transmitter may comprise, for example, a light emitting diode (LED), a laser, a laser diode or spatial light modulator (SLM) devices with a combination of a dispersive element. Examples of the type of suitable SLM devices that could be employed are: Digital Micromirror Device (DMD) at the heart of DLP displays or LCoS Displays (Liquid crystal on silicon).

Emitted light of the light transmitter may be selected so that the emitted light is not visible for an observer eye. In theory visible range is somewhere between 380-780 nm however there might be lights of 730 nm that people cannot see and can be also used.

In an embodiment, a custom RGB camera may be used for detection that is modified to also detect near-infrared (NIR) light with visible (VIS) cut off filter coupled.

Figure 3:
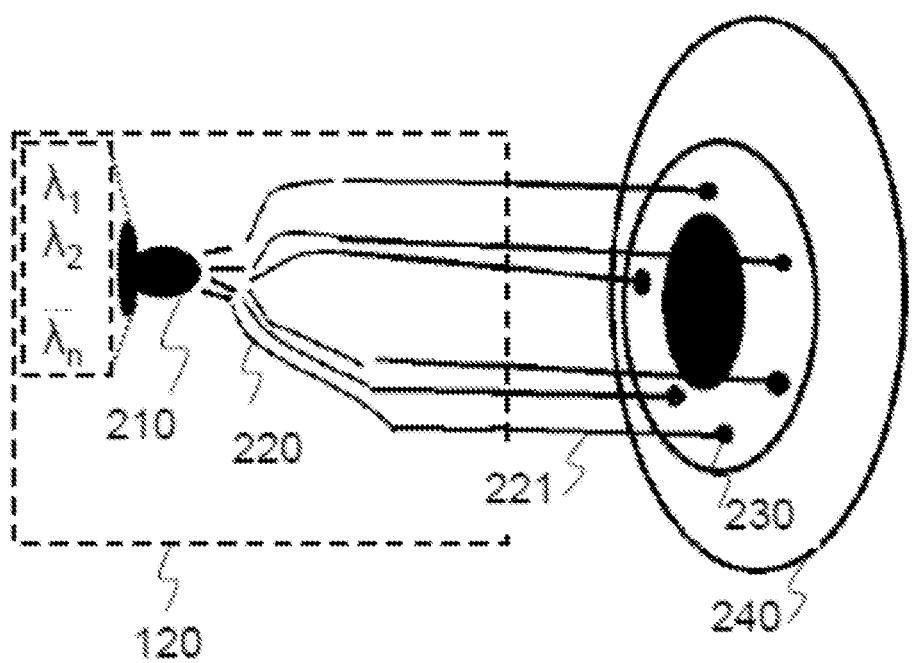
FIG. 3 shows another schematic drawing of generating a dynamic glint pattern/dynamic light beam in an example embodiment.

FIG. 3 shows another schematic drawing of a generating dynamic glint pattern or a dynamic light beam that enhance selected regions of the eye in an example embodiment.

An apparatus 120 is configured to determine gaze direction information based on a glint pattern/based on information from the surface of an eye. The apparatus 120 comprises a light source 210 for forming illuminating light 221 to an eye region 240 of a user. In an embodiment, the apparatus 120 comprises a spectrally adjustable light source 210 for forming light 221 to uniformly illuminate one or more regions or an eye of a user 240. Optical elements 220, such as freeform optical elements, are configured to guide and form the illuminating light 221 from the light source 210 to the eye region 240, wherein the illuminating light is configured to be dynamically adjustable to generate a dynamic glint pattern 230 on the eye region 240. In an embodiment, optical element(s) 220 are configured to collect and to intermix all emitted components of the light ($\lambda_1$, $\lambda_2$, ... $\lambda_n$). The SPD of newly formed light beam 221 from the light source 210 is being homogenized by means of optics 220 and illuminates uniformly one or more regions or an entire eye of a user 240 and concomitantly creates glint(s) 230 on the eye.

In an embodiment, each dynamic light beam 221 may be configured to have a specified intensity and spectral power distribution adjustable based on optical properties of the eye, for example.

In an embodiment, optics, such as freeform optics, may be used to adjust the light/newly formed light beam 221 to create a pattern on the eye. Light may be controlled by an algorithm, e.g. via a current driver that then controls the light transmitter(s) to generate light with different SPD (spectral power distribution) unique for each user or unique for group of users (e.g. eyes with similar optical properties).

FIG. 3 embodiment involves optical element(s), such as light guides, glass/plastic optical fibres, homogenizing rods 220 that are used as a light guide/to intermix the emitted components of the light source 210 ($\lambda_1$, $\lambda_2$, ... $\lambda_n$) and to guide a newly formed light beam 221 in order to shape the pattern of glints 230 appearing on the cornea 240.

Formed glint pattern shape 230 can be tracked even when the eye 240 is partially occluded or pointed away from the sensor, such as the camera (not shown). Enhanced system performance is achieved while ensuring eye safety limits and efficient energy consumption. Furthermore, person-adapted illumination and environment-adapted illumination are enabled.

The light guides, such as glass/plastic optical fibres, 220 are configured to guide and form illumination of the eye region 240. Formed shape of the glint pattern 230 can be adjusted and made unique. One source of illumination 210 may be used and the light is shaped and divided using the light guides, such as glass/plastic optical fibres, 220. Thus the radiation reaching the eye 240 is easily controlled and kept within standard limits. The unique optimized glint pattern 230 simplifies and enhances eye-tracking algorithm and make the solution more robust. In an embodiment, the light guides, such as glass/plastic optical fibers, 220 are configured to collect, intermix emitted components and to guide newly formed illumination illuminating one or more regions or an entire eye of a user 240. Formed shape of the concomitantly created glint(s) 230 can be adjusted and made unique. One spectrally tunable source of illumination 210 may be used and the newly formed SPD of the light is shaped and divided using the light guides, such as glass/plastic optical fibres, 220. Thus the radiation reaching the eye 240 is easily controlled and kept within standard limits. The unique optimized dynamic light beam illuminating the eye together with concomitantly generated glint(s) on 230 simplifies and enhances eye-tracking algorithm and make the solution more robust.

Furthermore, an optimized spectrum of illumination and/or an adaptive lighting of the light source 210 may be provided to create spectrum of illumination/optimized spectral power distribution. The adaptivity may take into account surrounding light conditions and optical and/or physiological properties of each individual's eye regions 240. The illumination by the light source 210 can be adapted to each user in order to provide the best final system performance. Settings are stored and can be loaded anytime. The illumination is also optimized with an imaging/photosensitive sensor (not shown) used.

The illustrated apparatus 120 fits well for wearable non-tethered devices where energy consumption is important and surrounding incident light conditions are changing.

In an embodiment, the light source 210 may comprise a plurality of transmitters (using radiance range that eye is not responding to), for example infrared LED's, at least one of them is configured to emit light in different spectral bands, and spectral power distribution of at least one transmitter may be adjusted based on the settings. At least one of the transmitters, such as LED's, may be configured to emit light with wavelength between 900-2600 nm or 1000-2600 nm.

Optical elements 220, such as freeform optics, may be used for pattern shaping of a newly formed light beam 221 and generation based on a light source. The light source allows to include one light transmitter (e.g. laser, LED, diode laser, SLM devices with a combination of a dispersive element) or several transmitters. Patterns can be adjusted by using programmable freeform optical elements, for example, or by combining optics with multifocal programmable lenses.

In an embodiment, the light source 210 (transmitter) is configured to be dynamically adjustable by a current/voltage level that is generated based on the control algorithm.

In an embodiment, the light source 210 comprises a plurality of transmitters that may emit light in different spectral bands (as illustrated by different wavelengths $\lambda_1$-$\lambda_n$). Combination of one or more transmitters at specified radiance level result in spectral power distribution (SPD) that is optimized for obtaining the best results e.g., contrast enhancement for the user eye.

In an embodiment, a powerful transmitter can be used that combines several spectral bands and may further utilize (freeform) optics to determine several glints on the eye. Alternatively, several separate transmitters may be utilized to emit designed energy at different spectral bands and repeated to concomitantly produce glint(s) pattern that is reflected from the eye (enables gaze detection).

In an embodiment, (freeform) optics may comprise optical fiber or implemented without optical fiber. Optical fibers may be used to intermix emitted components and for pattern shaping, for example.

A number of light transmitters or position of fibres create pattern itself (concomitantly), thus in some cases the pattern can be shaped by the fibres/transmitters, however then the pattern is not necessarily dynamic. However, even such a static pattern may be adjusted by arranging an additional lens that is configured to focus the pattern on the eye.

Figure 4:
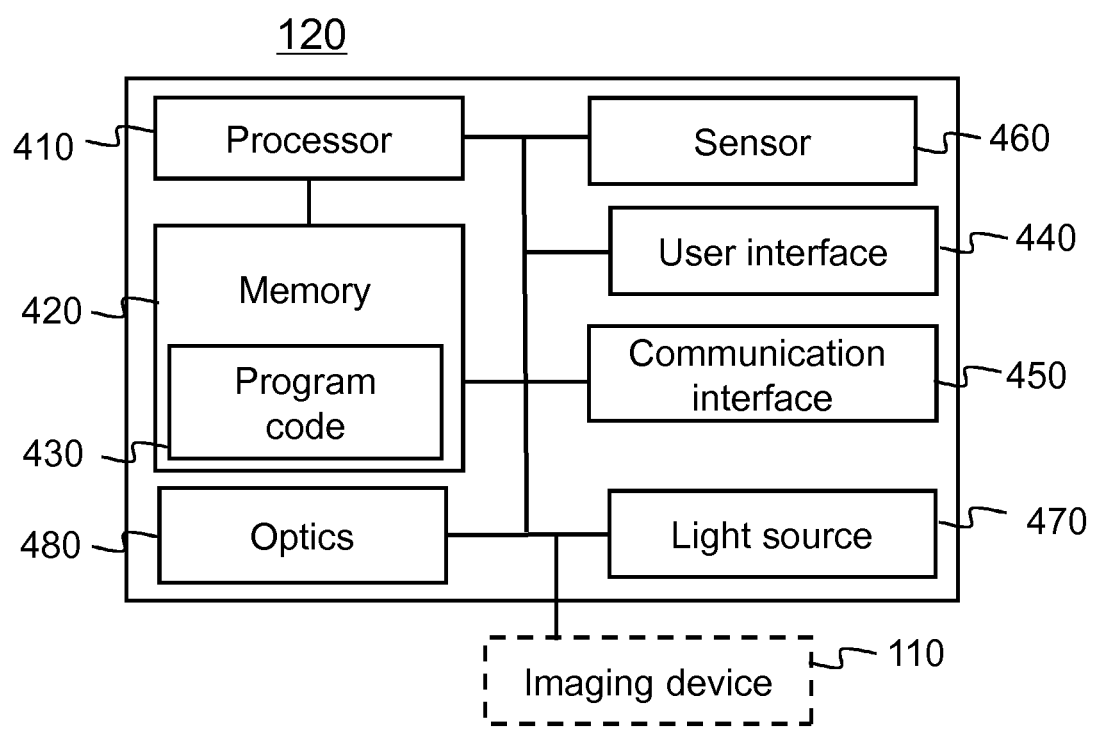
FIG. 4 shows a block diagram of an apparatus of an example embodiment.

FIG. 4 shows a block diagram of a client device 120 of an example embodiment. In an embodiment, a sensor 460 may be implemented as a separate device communicating via the communication interface 450 with the client device 120, or as an integrated sensor 460 within the device 120. The user interface 440 may be implemented also in another device connected via a communication interface 450 to the device 120. Such device may comprise a mobile phone, a smart-phone, or a tablet, for example. In an embodiment, the device 120 may communicate with a plurality of sensors 460, both internal and external sensors, and of a plurality of users. In an embodiment, the sensor 460 may also comprise a camera for capturing multimedia data to be submitted to the server apparatus 130, 131 as user data, gaze detection related data, for example.

The general structure of the device 120 comprises a user interface 440, a communication interface 450, a processor 410, and a memory 420 coupled to the processor 410. The device 120 further comprises software 430 stored in the memory 420 and operable to be loaded into and executed in the processor 410. The software 430 may comprise one or more software modules and can be in the form of a computer program product. Not all elements of FIG. 4 are necessary but optional for the portable apparatus 120, such as the sensor 460.

In an embodiment, a proprietary application 124 of FIG. 1, such as a gaze detection application, is a computer-implemented client software application 430 to record data. The proprietary application may also comprise a computer-implemented web browser application. The electronic diary may also comprise a combination of a client software application and a browser application.

The processor 410 may be, e.g., a central processing unit (CPU), a microprocessor, a digital signal processor (DSP), a graphics processing unit, or the like. FIG. 4 shows one processor 410, but the device 120 may comprise a plurality of processors.

The memory 420 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The device 120 may comprise a plurality of memories. The memory 420 may be constructed as a part of the device 120 or it may be inserted into a slot, port, or the like of the device 120 by a user. The memory 420 may serve the sole purpose of storing data, or it may be constructed as a part of an apparatus serving other purposes, such as processing data.

The user interface 440 may comprise circuitry for receiving input from a user of the device 120, e.g., via a keyboard, a touchpad, a motion sensor, a touch-screen of the device 120, speech recognition circuitry, gesture recognition circuitry or an accessory device, such as a headset or a remote controller, for example. Furthermore, the user interface 440 may comprise circuitry for providing output for the user via a display, a speaker, a touch-sensitive display or a tactile feedback device, for example.

In an embodiment, a user may speak during the gaze detection and the speech is automatically converted to feedback information for the system. Thus feedback is always up-to-date and accurate.

The communication interface module 450 implements at least part of data transmission. The communication interface module 450 may comprise, e.g., a wireless or a wired interface module. The wireless interface may comprise such as a WLAN, Bluetooth, infrared (IR), radio frequency identification (RF ID), NFC, GSM/GPRS, CDMA, WCDMA, LTE (Long Term Evolution) or 5G radio module. As the radio technologies are evolving and new replacing systems being developed, the new developed technologies can be used for the communication interface module 450 in view of different embodiments disclosed. The communication interface module 450 may also comprise non-RF connection, such as Light Fidelity (Li-Fi). The wired interface may comprise such as universal serial bus (USB), for example. The communication interface module 450 may be integrated into the device 120, or into an adapter, card or the like that may be inserted into a suitable slot or port of the device 120. The communication interface module 450 may support one radio interface technology or a plurality of technologies. The communication interface module 350 may support one wired interface technology or a plurality of technologies. The device 120 may comprise a plurality of communication interface modules 450.

In an embodiment, the communication interface module 450 may comprise location modules for tracking location of the device 120. Such location modules may comprise a module for satellite based global positioning system (e.g. GPS), a module for cellular based positioning system, a module for wireless non-cellular positioning system (e.g. Wi-Fi) or a module for hybrid positioning system, for example.

In an embodiment, the communication interface 450 with a satellite based global positioning system (e.g. GPS) may detect altitude of the user to provide an estimate of thinness of air.

A skilled person appreciates that in addition to the elements shown in FIG. 4, the device 120 may comprise other elements, such as microphones, speakers, sensors, cameras, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like. Additionally, the client device 120 may comprise a disposable or rechargeable battery (not shown) for powering when external power if external power supply is not available.

In an embodiment, the algorithm(s) and computer program codes controlling illumination/dynamic light beam and/or patterns/glint detection can be arranged within a chip/chipset that may be included to client device 120.

In an embodiment, the client device 120 comprises speech or gesture recognition means. Using these means, a predefined phrase or a gesture may be recognized from the speech or the gesture and translated into control information for the device 120.

In an embodiment, an imaging device part of the apparatus 120 may be implemented as an imaging device 110, such as a fiber-based imaging bundle. The imaging device 110 may transfer an image out from an gaze detection device 110. The size of gaze detection device can be significantly reduced and an imaging part can be out from the gaze detection device.

Size of gaze detection device may be thus reduced and no dichroic filter (or hot mirror) element is required at all. Power supply for the imaging device 110 can be separated for illumination 110 and recording 120 parts. Efficient energy consumption is enabled especially in case of head mounted devices. Furthermore, the device is less fragile and image spatial resolution can be enlarged since the recording unit does not have to be small in order to fit gaze detection device's casing.

In an embodiment, an apparatus 110, 120 may be provided as an additional gaze detection device that can be coupled to an ocular without any modification to a see-through device, such as a microscope, for example. The device 120 may be arranged with mechanics to enable an easy attachment to any optical device, such as an ocular. Distance between the human eye and ocular may be minimized by such solution. Light that is unrecognizable by user's eye (e.g. near infrared light) is transmitted to the eye and the light reflects back to a photosensitive sensor, such as a camera. However the visible light that comes through the optical system of the apparatus, e.g. through an ocular, can be transmitted normally to the eye without being disturbed by any element of the device. A video camera with a higher frame rate is adapted to detect the transmitted light from the light source, which will allow the detection of the glint pattern/dynamic light beam illuminating the eye together with concomitantly generated glint(s) on the observer's eye.

Thus the external gaze detection device 110, 120 can enhance old microscopes and such simplified solution does not require modification for the microscopes (any see-through or the near-to-eye optical device) at all. Additional eye tracking device 110, 120 may be used for rapid detection for eye movement and gaze information can be used in a wide variety of different applications, such as hands-free control of a microscope, for example.

Typically used light sources 470 are LED's, laser diodes, laser, with spatial light modulator (SLM) devices with a combination of a dispersive element. Examples of the type of suitable SLM devices that could be employed are: Digital Micromirror Device (DMD) at the heart of DLP displays or LCoS Displays (Liquid crystal on silicon). Illumination typically contains one or more IR LEDs 470 that concomitantly reflect back from the surfaces of the cornea and the lens (referred as glint). The detection/recordings of the glint and pupil is made by a sensor 460, such as a photodetector(s)/photosensor(s), like a CCD/CMOS imaging sensor(s), for example. Due to glint detection the measurements are independent from movement of user's head.

The algorithm 430 measures the eye orientation from the relative position of the centre of the pupil and the glint. The position between these two is further used to specify the exact position of gaze of a user.

Figure 5:
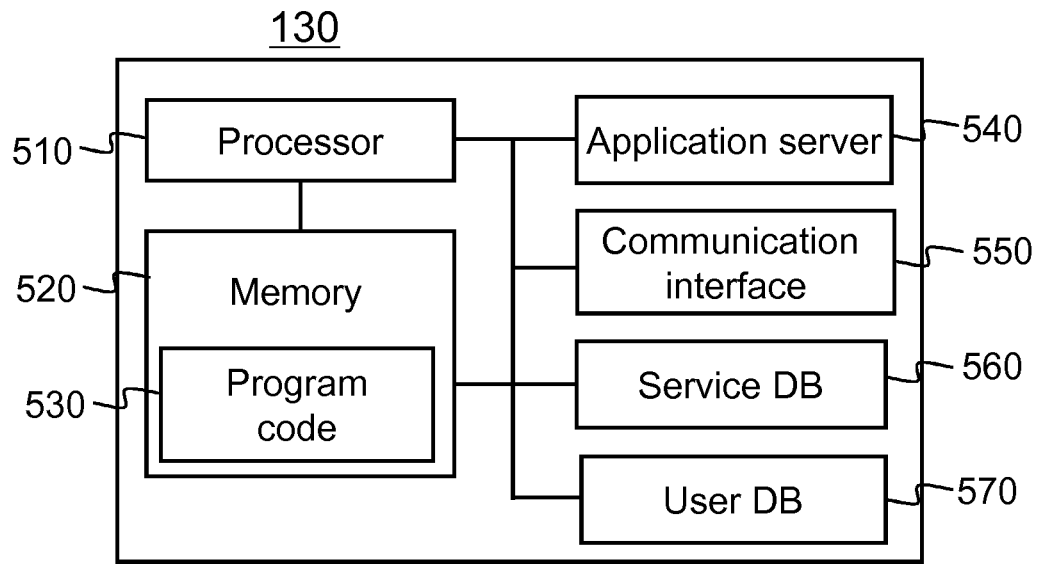
FIG. 5 shows a block diagram of a cloud server apparatus of an example embodiment.

FIG. 5 presents an example block diagram of a server apparatus 130 in which various embodiments of the present disclosure may be applied. All elements described in FIG. 5 are not necessary to be implemented in the same apparatus 130.

The general structure of the server apparatus 130 comprises a processor 510, and a memory 520 coupled to the processor 510. The server apparatus 130 further comprises software 530 stored in the memory 520 and operable to be loaded into and executed in the processor 510. The software 530 may comprise one or more software modules and can be in the form of a computer program product. The software 530 may comprise a server application 133 of FIG. 1.

The processor 510 may be, e.g., a central processing unit (CPU), a microprocessor, a digital signal processor (DSP), a graphics processing unit, or the like. FIG. 5 shows one processor 510, but the server apparatus 130 may comprise a plurality of processors.

The memory 520 may be for example a non-volatile or a volatile memory, such as a read-only memory (ROM), a programmable read-only memory (PROM), erasable programmable read-only memory (EPROM), a random-access memory (RAM), a flash memory, a data disk, an optical storage, a magnetic storage, a smart card, or the like. The server apparatus 130 may comprise a plurality of memories. The memory 520 may be constructed as a part of the server apparatus 130 or it may be inserted into a slot, port, or the like of the server apparatus 130 by a user. The memory 520 may serve the sole purpose of storing data, or it may be constructed as a part of an apparatus serving other purposes, such as processing data.

The communication interface module 550 implements at least part of data transmission. The communication interface module 550 may comprise, e.g., a wireless or a wired interface module. The wireless interface may comprise such as a WLAN, Bluetooth, infrared (IR), radio frequency identification (RF ID), GSM/GPRS, CDMA, WCDMA, LTE (Long Term Evolution) or 5G radio module, for example. As the radio technologies are evolving and new replacing systems being developed, the new developed technologies can be used for the communication interface module 550 in view of different embodiments disclosed. The communication interface module 550 may also comprise non-RF connection, such as Light Fidelity (Li-Fi). The wired interface may comprise such as Ethernet or universal serial bus (USB), for example. The communication interface module 550 may be integrated into the server apparatus 130, or into an adapter, card or the like that may be inserted into a suitable slot or port of the server apparatus 130. The communication interface module 250 may support one radio interface technology or a plurality of technologies. Configuration information between the client device 120 and the system server 130 may be transceived using the communication interface 550. Similarly, account creation information between the system server 130 and a service provider may be transceived using the communication interface 550.

An application server 540 provides application services e.g. relating to the user accounts stored in a user database 570 and to the service information stored in a service database 560. Different application services may be provided to different users. The application server 540 may comprise a server application 133 of FIG. 1.

A skilled person appreciates that in addition to the elements shown in FIG. 5, the server apparatus 130 may comprise other elements, such as microphones, displays, as well as additional circuitry such as input/output (I/O) circuitry, memory chips, application-specific integrated circuits (ASIC), processing circuitry for specific purposes such as source coding/decoding circuitry, channel coding/decoding circuitry, ciphering/deciphering circuitry, and the like.

Figure 6:
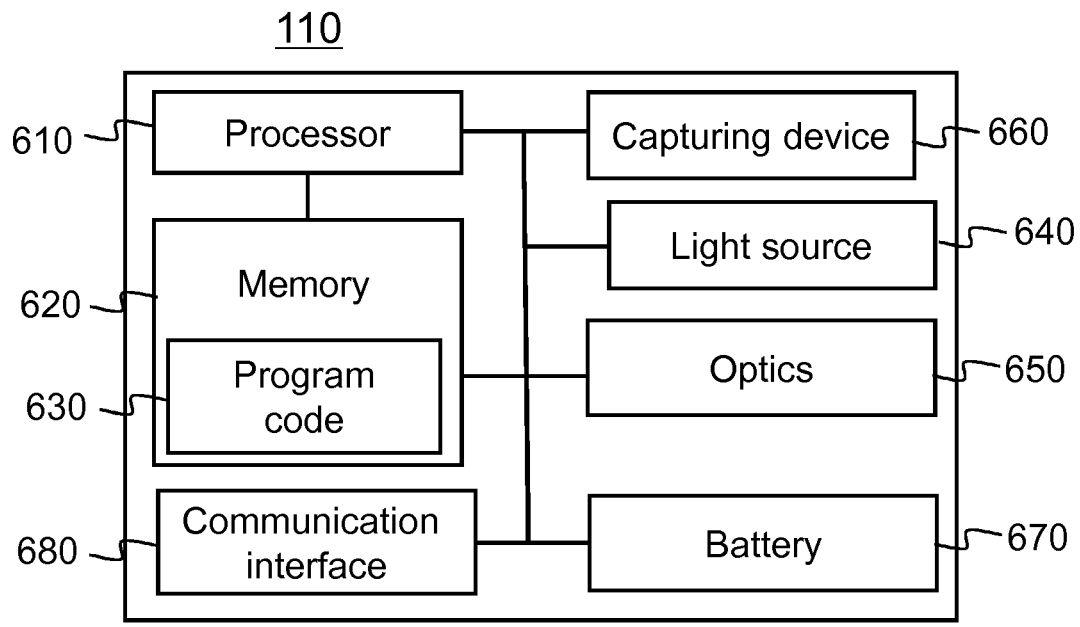
FIG. 6 shows a block diagram of a imaging device of an example embodiment.

FIG. 6 shows a block diagram of an imaging device 110 of an example embodiment.

The imaging device 110 is configured to determine gaze direction information based on a glint pattern/based on information from the surface of an eye. The imaging device 110 may comprise a first battery 670 configured to power the imaging device 110 but the device 110 may also be powered externally via a cable, for example. The imaging device 110 further comprises a light source 640 for forming illuminating light to an eye region of a user/designed light illuminating an eye region of the user, and optical element(s)/freeform optical elements 650 configured to collect and intermix the emitted components of the light ($\lambda_1, \lambda_2, \ldots \lambda_n$) and to guide and form uniformly illuminating light from the light source 640 to the eye region, wherein the SPD of illuminating light is configured to be dynamically adjustable to generate a dynamic glint pattern/unique dynamic light beam together with concomitantly crated glint(s) on the eye region. Furthermore, a gaze detection component 660 is configured to capture an image of the eye region.

The imaging device 110 further comprises at least one memory 620 including computer program code 630, the at least one memory 620 and the computer program code 630 are configured to, with the at least one processor 610, cause the device 110 to receive settings comprising at least one of the following: environmental information of the apparatus and user profile information (e.g. eye's optical properties), to adjust the dynamic glint pattern/dynamic light beam based on the settings, and to capture an image of the eye region using the capturing device 660. The captured image of the eye region is transmitted to the apparatus 120 for generating reflection eye data, and further for generating the gaze direction information based on the reflection eye data.

The imaging device 110 further comprises a communication interface 680 for transceiving information with an apparatus 120 (see FIG. 1), the apparatus 120 comprising a second battery configured to power the apparatus, a sensor that is configured to determine reflected glint pattern of the eye region/reflected dynamic light beam illuminating the eye together with concomitantly created glint(s) on the eye region based on the image of the eye region and generate reflection eye data, maintain settings comprising at least one of the following: environmental information of the apparatus; and user profile information; adjust the dynamic glint pattern/dynamic light beam based on the settings; receive the reflection eye data; and generate the gaze direction information based on the reflection eye data.

In an embodiment, the optical system 650 may comprise an imaging light guide between a user eye and a sensor. The light guide may comprise a borescope tube. Borescope is an optical device comprising a rigid or flexible tube with an objective lens on one end linked with other end by a relay optical system in between.

FIG. 7 shows a flow chart of a process according to an example embodiment of the present disclosure.

A computer implemented method starts in step 710. The computer-implemented method is suitable for determining gaze direction information based on a glint pattern/based on information from the surface of an eye.

In step 720, settings comprising at least one of the following: environmental information of an apparatus, and user profile information, are maintained. The user profile information may comprise, for example, feature contrast information. In an embodiment, the user profile information may comprise optical properties of user's eye and/or SPD settings to maximize contrast between selected features, and/or data from spectral calibration, and/or image information of selected eye features.

In step 730, a dynamic glint pattern/dynamic light beam is adjusted based on the settings, wherein optical elements, such as freeform optical elements, are configured to guide and form illuminating light from a light source to eye region, and the illuminating light is configured to be dynamically adjustable to generate the dynamic glint pattern on the eye region. Both glint pattern formation and spectral power distribution (SPD) of the glint pattern may be adjusted. In an embodiment, optical elements are configured to collect and intermix all emitted components of the light ($\lambda_1, \lambda_2, \ldots \lambda_n$) and to guide newly formed illuminating light from a light source to eye region, wherein the SPD of illuminating light is configured to be dynamically adjustable to generate the dynamic light beam to enhance contrast/captured image information between selected features on the eye region. Both spectral power distribution of dynamic light beam together with concomitantly created glint(s) illuminating the eye and glint pattern formation may be adjusted.

In an embodiment, the optics, such as freeform optics, may be used to adjust the pattern formation and the light source may be used to adjust the pattern SPD. In an embodiment, the optics element(s) may be used to adjust the pattern formation and the light source may be used to adjust the SPD to enhance system performance.

In step 740, reflection eye data is received from a sensor configured to capture reflected glint pattern of the eye region/reflected dynamic light beam together with concomitantly created glint(s) on the eye region and generate the reflection eye data.

In step 750, the gaze direction information is generated based on the reflection eye data.

In step 760, the method ends,

FIGS. 8a-c show schematic drawings of a gaze detection device (eye tracker) used for generating and detecting dynamic glint pattern/dynamic light beam of example embodiments.

An apparatus 120 is shown for determining gaze direction information based on a glint pattern/based on a dynamic light beam together with concomitantly created glint(s). The apparatus 120 illustrates the effective feature that enables an easy attachment to an ocular 810, decreasing the distance between the human eye 820 and the ocular 810. Light emitted by a light source 470 is directed to the eye 820 and reflected back to the camera 460. However the visible light 805 that is coming through the ocular 810 can be transmitted normally to the eye 820 without being disturbed by any element of the apparatus 120. A video camera 460 with a higher frame rate may be adapted to detect light (e.g. near infrared light NIR), which will allow the detection of the observer's eye 820.

In some cases there might be arranged a dichroic filter (or hot mirror) inside the apparatus 120. Then the light source 470 and the camera 460 are typically focused on the central part of the filter/mirror. The filter/mirror transmits visible spectrum (VIS) light to the eye and also reflects infrared (IR) light from the eye to the camera 460.

The gaze detection apparatus 120 can be easily attached to a binocular 810 of a neurosurgical microscope, for example. The dimension and weight of the apparatus 120 are minimized for obtaining better coupling to the binocular 810 without any microscope modification/without any modification of device optics.

In an embodiment, the gaze detection apparatus 120 may be attached to an eye-piece 815 of the optical apparatus 810. The eye-piece 815 may be made of rubber, for example. The gaze detection apparatus 120 may comprise threads 825 for coupling it to the optical apparatus 810. Optionally the gaze detection apparatus 120 may have threading/mounting 825 suitable for a dedicated model of a see-through optical apparatus 810. The gaze detection apparatus 120 may also be attached by "click-on" mechanical elements that fit the see through optical apparatus 810. In some cases, the gaze detection apparatus 120 can be also built-in the eye-piece guard rubber element 815 or in the "distance tube" in case of microscope, for example.

In an embodiment, input data for calibration of the gaze detection apparatus 120 and the control algorithm may be processed. A light source 210, 470 may be calibrated in order to obtain input data for the algorithm that controls the light source 210, 470 to get an unique optimized spectral power distribution to maximize contrast between eye features when operating the gaze detection apparatus 120. For example, a unique calibration of the apparatus 120 may comprise scanning the eye of the user through all spectral bands included into the light source 210, 470 ($\lambda_1, \lambda_2, \ldots \lambda_n$). Scanning may comprise steps to turn ON $\lambda_1$ and take image by the imaging sensor 460, then move to $\lambda_2$ and acquire another image. This procedure may be repeated for all spectral bands. As a result image is captured for each spectral band (images may be captured very fast without user being noticed of any spectral band changes). (Thus it is provided a spectral device solution inside the eye tracker or the gaze detection apparatus.) Such approach delivers both spectral/optical signatures and spatial information that can result in so called spectral cube, typically used in multispectral imaging. Captured set of images is dependent on the light source bands ($\lambda_1, \lambda_2, \ldots \lambda_n$) and imaging sensor's spectral properties. Therefore, spectral properties for both the imaging sensor and spectral bands of the light transmitter may be utilized if available before starting the calibration. However, this approach/the solution presented herein will work also without preliminary knowledge of the imaging sensor or without exact data related to the spectral bands emitted from the transmitters due to reference element.

Next, the algorithm detects e.g., iris, pupil, or other features of the eye and furthermore the contrast between selected features may be compared. Contrast is used here, however other properties of the image like brightness, dynamic range, high dynamic range, etc. can be also compared. The image quality index or several indexes are set as default by the calibration software or by a user. In an embodiment, the algorithm detects selected features of the eye e.g., iris, pupil and compares image information e.g., contrast between selected features. For this example, contrast is used as the attribute of an image, however herein, other example attributes may be used to measure the image information e.g., contrast, brightness, luminance level, and other qualities of the feature regions contingent on the illumination distribution. The selection of attribute(s) used at this step are set as a default within the calibration software or are specified by a user.

In the next step of the algorithm, depending on features of the interest, the best spectral bands are determined. In an embodiment, depending on features of the interest being detected automatically or marked by a user, the most significant spectral components of the light are determined. In an embodiment, at least one image is determined to result with better contrast between iris and pupil to compare with other images for an example eye type. In an embodiment, at least one image is determined to provide better contrast between e.g., iris and pupil to compare with other image(s) acquired for the same eye. Here, value of the chosen attribute(s) from the selected image is defined. Herein, several common examples for defining contrast value are e.g., Michelson, Weber, and Root mean square contrast (RMS). It may be that a plurality of images are selected based on contrast value comparison. In case of the other user the result may be significantly different and another contrast values would be obtained.

Next, in an embodiment the algorithm determines contrast between the selected (best) images and defines the contrast index. Contrast index is then converted to the intensity of the spectral band in the transmitter. Conversion between contrast values and spectral band intensity can be linear or nonlinear, wherein also optimization methods could be involved. In an embodiment, the algorithm compares and sorts previously calculated attribute(s) e.g., contrast between selected features from the most significant images, and produces index list associated with the significance of each spectral component of the dynamic light beam for image attribute(s) enhancement. Index list is then converted to the intensity of the spectral band in the transmitter(s). Conversion between defined image attribute(s) values and spectral band intensity can be linear or nonlinear, wherein also optimization methods could be involved.

The indexing step/obtaining index list and step of taking reference images for each spectral band could be repeated within the algorithm in case the algorithm cannot detect some features (features can be set automatically or manually), for example. Furthermore after conversion step, additional steps/process steps may be included e.g., comparison of the image contrast resulting from the combination of spectral bands in conversion against each image captured for a single band/comparison of the image attribute(s) value resulting from the defined combination of the spectral bands against image attribute(s) value from each image captured for a single spectral band (reference images). In case determined results are not satisfactory enough to compare with the reference images, the calibration steps may be repeated or the best/most significant single band may be used.

As a result, if all steps of the calibration algorithm are performed correctly, the image obtained while the eye being illuminated based on calibration data has an improved contrast between dedicated pair of features for e.g. iris and pupil. In an embodiment, if all steps of the calibration algorithm are performed correctly, the image acquired while the eye being illuminated with a dynamic light beam based on calibration data has enhanced image attribute(s) e.g., an improved contrast between dedicated pair of features for e.g. iris and pupil. Herein, the enhancement of the image is obtained in real-time without any additional image processing.

Such calibration data provides input data for control algorithm steps that generate information about intensity level of each spectral band to be used (e.g., $\lambda_1 \rightarrow 100\%$, $\lambda_2 \rightarrow 2\%$, $\lambda_3 \rightarrow 0\%$, $\lambda_4 \rightarrow 22\%$). Data can be determined for each user, stored and reused. Such data can be also obtained for specific group of users with different eye optical properties etc. and provided through the cloud service 130-133, 150-151.

Using the calibration procedure it is possible to obtain optical properties of the eye 820 to get characteristic information of which spectral bands should be turned ON/OFF and at what intensity level when operating the gaze detection. It is possible to adjust and continuously update settings based on the calibration.

An optimized spectral power distribution (SPD) for each eye optical property may be determined from the previous research results so a new user may just provide selection information for the type of the eye and optimized spectral power distribution (SPD) data is loaded for the gaze detection apparatus 120. In an embodiment, an optimized spectral power distribution (SPD) of the dynamic light beam is dependent on each eye optical property and may be determined from the previous research results thus, a new user may just provide selection information for the type of the eye e.g., eye pigmentation and optimized spectral power distribution (SPD) data is loaded for the gaze detection apparatus 120.

Spectral power distribution (SPD) of a dynamic light beam and concomitantly created glint(s) can also be made manually adjustable by the user to be easily controlled by the user to give the best results as personal feedback.

In an embodiment, in relation to the calibration algorithm steps discussed above, the illumination of a user eye may contain e.g. 5-spectral bands (e.g. between 600-1200 nm). The wavelength peak and the spectral distribution for each emitted band is beforehand defined/measured. The peaks may be, for example, 650 nm, 750 nm, 900 nm, 1000 nm, 1150 nm. A set of images is captured in the same way as explained above.

Each spectral band $\lambda_1$-$\lambda_5$ (order of spectral band to be ON does not matter) is turned ON and the images are captured for each spectral band $\lambda_1$-$\lambda_5$. Since the intensity and the peak wavelength of each spectral band are known, the spectral properties of the imaged object can be determined. This procedure generates information within the algorithm about amount of the reflected light from the object in the field of view of the imaging sensor (an eye). Herein, information of the sensitivity of the sensor is also relevant to obtain correct results.

A further algorithm step calculates/generates calculated distances of reflectance information (e.g. between iris and pupil with different spectral bands/amount of reflected light from iris and from pupil at different spectral bands) that provide the algorithm input information about similarity between optical properties of two (or more) selected features (features can be detected automatically or manually by user). In case of pupil and iris, spectral properties of the selected points are analysed and based on the spectral properties of two or more features are calculated, the algorithm generates information about the biggest/smallest differences between all features for the spectral bands $\lambda_1$-$\lambda_5$. In an embodiment, in case of pupil and iris as an example features, spectral properties of the selected points are analysed and the distances between measured reflectances are calculated. The algorithm generates information about the biggest/smallest signal differences between all features for the spectral bands $\lambda_1$-$\lambda_5$.

For example, distance corresponding to the reflectivity of the light for spectral band ($\lambda_1$-$\lambda_5$) may be correlated with the intensity of the spectral band that should be used. However, there are many other methods in order to differentiate two or more spectral features that can be used.

After generating the intensity list for spectral bands $\lambda_1$-$\lambda_5$, the optimized illumination may be used for gaze detection.

The produced illumination can be validated against previously obtained set of images for each $\lambda_1$-$\lambda_5$ spectral band. In case contrast/chosen image attribute between features (or between contrast/image qualities/image attributes of the total image) is not improved one of the $\lambda_1$-$\lambda_5$ spectral bands providing the best results may be selected.

In an embodiment, a multi-wavelength illumination using at least one dynamic light source comprising at least one light transmitter may be used. The multi-wavelength illumination may be used for both acquiring spectral properties of user's eye and then to use the acquired data as an input for the control algorithm that results in optimized illumination for real-time contrast/image information enhancement.

No matter contrast is used here as an example, other properties of the image like brightness, dynamic range, high dynamic range, etc., may also be included into the algorithm and can be optimized accordingly to the settings. Accordingly, other attributes may be used to measure the image information e.g., brightness, luminance level, and other qualities of the feature regions contingent on the illumination distribution. Single or several image attributes may also be included into the algorithm and can be optimized accordingly to the settings.

In an embodiment, in relation to the calibration algorithm steps discussed above, reference data for calibration may be provided.

In an embodiment, for the calibration phase, the user may be requested to use standard reference caps or plates for suppressing the image imperfections and to specify the intensity and the light distribution all over the field of view of the camera. The plate 830 may be arranged, for example, on top of the gaze detection apparatus 120 or the eyepiece 815, depending on the implementation. The plates 830 may comprise, for example, black plate and white plate that may be exchangeably arranged as standard reference for camera/sensor/image calibration.

In an embodiment, instead of a plate, a ring (e.g. white or other colour detectable by the camera) could also be used with a pre-defined colour so that the camera is capable of detecting it as a reference.

Standard reference plate(s) could be used for reference data measurements before the steps disclosed above for the calibration algorithm phase.

Standard reference plates 830 may be an optimal solution, however ocular (see-through optics) may be closed by any other non-transparent object (preferably white or black) from the top (where the user eye is typically located). In addition, in the design of the eye-tracker/gaze detection apparatus 120 or of a separate tool to be attached to the eyepiece guard, for example, a standard reference circle formation/plate of a ring shape that does not affect view for the user could be attached on the top layer of the eye-tracker casing or the eye guard. The standard reference circle formation/plate may be arranged in such way that light emitted from the transmitters would be reflected back from the reference formation/from the area of the reference plate to the camera to continuously provide information about light distribution and its variations. That could be used to control light intensity or to monitor the light intensity in the continuous data recordings. The solution presented herein, may be used for spectral and spatial correction of the light source and/or sensor caused by e.g., the temperature variations of the light source, non-uniform light distribution caused by misaligned optics element(s).

FIG. 8c illustrates an example of an image 840 captured by proposed setup including a calibration ring 831 and how the image could look like.

In an embodiment, data from the set of calibration images including the calibration ring 831 when each spectral band $\lambda_1$-$\lambda_5$ is ON could be used for several purposes. Pixel values of the image 840 all over the area of the calibration ring 831 generates data about light distribution, light fluctuation, intensity of each spectral band, etc. This input data can be used for image correction, light source or glint control, or as input for calibration or control algorithms.

The calibration ring 831 may be arranged to the apparatus 120 as shown in FIG. 8*b* as element 830, for example. In such case, a region of the interest (ROI) of the scene 840 captured by the camera/sensor can be adjusted and therefore not every captured image frame 840 has to contain information about the calibration ring 831. After obtaining required calibration data, the ROI could be re-adjusted to provide image of the eye only, as illustrated by the dashed frame 841. Adjustment between frames sizes 840, 841 may be configured to be controlled by the calibration algorithm, for example. The calibration ring 831 can be applied as an additional ring-shaped element to be attached to a rubber piece or any near-to-eye or see-through device, or as painted area inside the eye tracker casing/body and both may be used in order to produce reference area 840, 841. Both methods allow non-invasive way of applying calibration data that may provide relevant input data for the proposed calibration algorithms.

Figure 9:
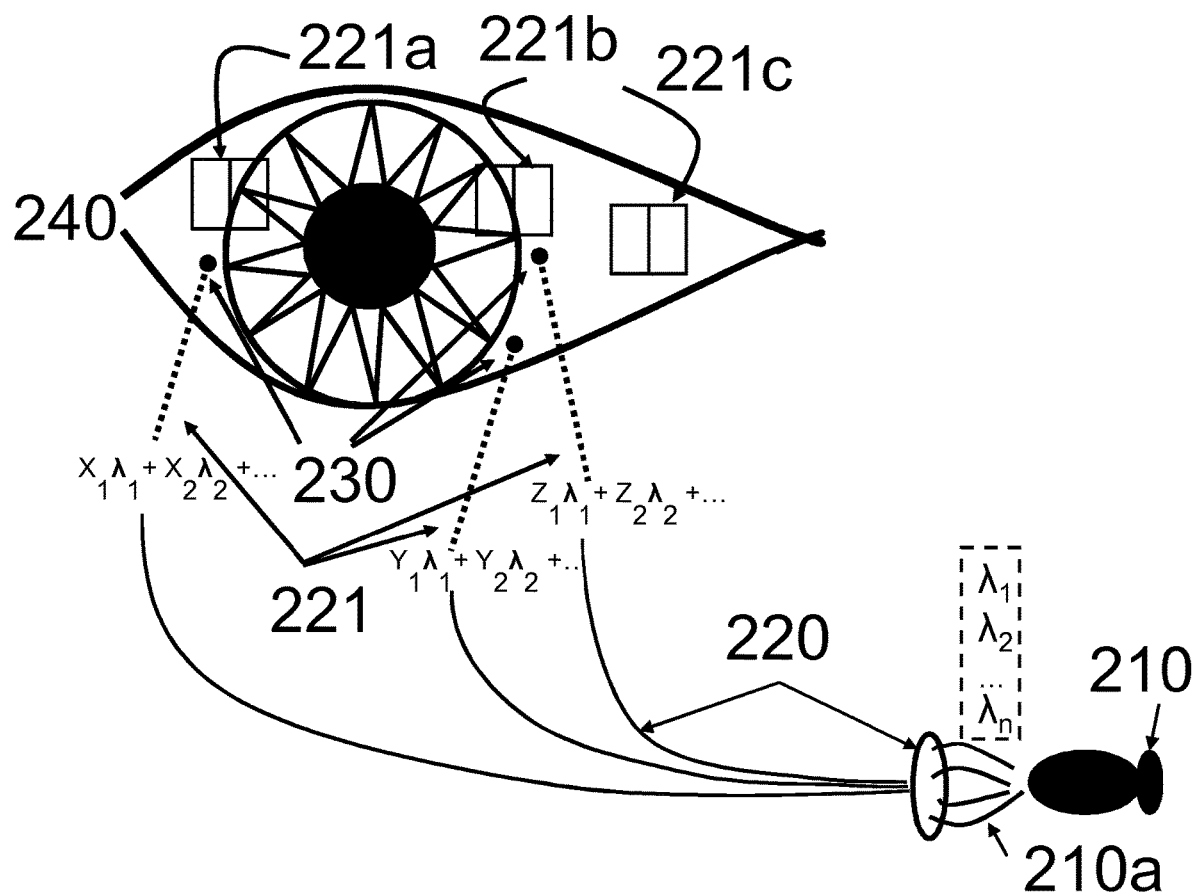
FIG. 9 shows a further example of generating a dynamic light beam in accordance with certain embodiments.

FIG. 9 shows a further example of generating a dynamic light beam in accordance with certain embodiments. The light source 210 comprises one or a plurality of transmitters (using radiance range that the eye 240 is not responding to), for example infrared LEDs. At least one of the transmitters is configured to emit light in different spectral bands, and spectral power distribution of at least one transmitter may be adjusted based on the settings. At least one of the transmitters, such as LEDs, may be configured to emit light with wavelength between 900-2600 nm. The light source allows to include one light transmitter (e.g. laser, LED, diode laser, SLM devices with a combination of a dispersive element) or several transmitters.

Emitted different spectral bands are illustrated by different wavelengths $\lambda_1$-$\lambda_n$. The separate components ($\lambda_1$-$\lambda_n$) are not collected, intermixed, guided/aligned onto the eye region yet, but this is done subsequently by optics to provide the best spectral homogeneity and to illuminate the eye uniformly.

Optical element(s) 220, such as an optical lens, optical fibers, waveguide, homogenizing rod, also freeform optics, is used to collect and to intermix all emitted components 210*a* of the light source 210. The spectral power distribution (SPD) of a newly formed (dynamic) light beam 221 is being homogenized by means of optics 220 and illuminates the eye 240.

As mentioned, newly formed (intermixed and aligned) dynamic light beam(s) 221 is(are) being homogenized by means of optics 220. Spectral distribution of the illuminating light 221 (illuminating light=dynamic light beam on the eye) is dynamically adjustable to produce a dynamic light beam 221 to enhance captured image information between/for selected features (221*a*, 221*b*, 221*c*) of the eye of the user in question.

For this example, SPD for feature 221*a* is $X_1\lambda_1+X_2\lambda_2+\ldots$, for feature 221*b* is $Y_1\lambda_1+Y_2\lambda_2+\ldots$, for feature 221*c* is $Z_1\lambda_1+Z_2\lambda_2+\ldots$, etc.

Here, the variables X, Y and Z stand for defined unique (unique for each selected feature 221*a*, 221*b*, 221*c* and each user) intensity level (e.g., level between 0-100%) of corresponding wavelengths $\lambda_1, \lambda_2 \ldots \lambda_n$ emitted from the light source 210.

Glint(s) 230 are the reflection on the cornea and are concomitantly created when illuminating the eye with the dynamic light beam(s) 221.

Both spectral and spatial properties of concomitantly formed shape of the glint(s) 230 can be adjusted and made unique. Patterns can be adjusted by using programmable freeform optical elements, for example, or by combining optics with multifocal programmable lenses, and/or any element mentioned in connection with reference numeral 220.

The spectral power distribution of light beam(s) 221 for selected features 221*a*, 221*b*, 221*c* was defined in this embodiment to provide real-time enhancement of contrast (or captured image information) from the eye.

Without in any way limiting the scope, interpretation, or application of the claims appearing below, a technical effect of one or more of the example embodiments disclosed herein is improved method and apparatus for detecting gaze information of a user. Another technical effect of one or more of the example embodiments disclosed herein is enhancement of captured image information, contrast as an example. Another technical effect of one or more of the example embodiments disclosed herein is generation of the optimal spectral power distribution of the light beam and concomitantly created glint(s) and detection of the user eye. Another technical effect of one or more of the example embodiments disclosed herein is more accurate glint pattern generation and detection of the user eye.

Another technical effect of one or more of the example embodiments disclosed herein is that more convenient user experience from the point of subject user is enabled.

Another technical effect of one or more of the example embodiments disclosed herein is that system and service is cost efficient and easy-to-use.

If desired, the different functions discussed herein may be performed in a different order and/or concurrently with each other. Furthermore, if desired, one or more of the before-described functions may be optional or may be combined.

Although various aspects of the present disclosure are set out in the independent claims, other aspects of the present disclosure comprise other combinations of features from the described embodiments and/or the dependent claims with the features of the independent claims, and not solely the combinations explicitly set out in the claims.

It is also noted herein that while the foregoing describes example embodiments of the present disclosure, these descriptions should not be viewed in a limiting sense. Rather, there are several variations and modifications, which may be made without departing from the scope of the present disclosure as defined in the appended claims.

However, claimed embodiments do not constitute a method step for treatment of the human or animal body by surgery or therapy. No functional relationship exists between the steps related to apparatus and any therapeutic effect of the apparatus on the body.

The invention claimed is:

1. An apparatus for determining gaze direction information, comprising:
   a light source configured for forming illuminating light to one or more regions of an eye of a user;
   optical element(s) configured to guide the illuminating light from the light source to the one or more regions of the eye, wherein the illuminating light is dynamically adjustable to generate a dynamic light beam on the one or more regions of the eye;

a sensor configured to capture reflected light from the one or more regions of the eye and generate reflection eye data;

at least one processor and at least one memory including computer program code; the at least one memory and the computer program code being configured, with the at least one processor, to cause the apparatus to:

maintain settings comprising user profile information;

adjust spectral power distribution of the light source based on the user profile information;

receive the reflection eye data;

generate the gaze direction information based on the reflection eye data; and conduct spectral calibration of the apparatus by performing at least the following steps:

scanning the one or more regions of the eye of the user through different spectral bands, or combinations of spectral bands, of the light source and capture an image by the sensor for each different spectral band;

comparing image attribute(s) of at least two captured images;

selecting at least one image based on the comparison;

one or more of defining an attribute value or creating an index list based on the significance of the selected image;

determining an intensity of at least one spectral band using one or more of the attribute value or index list; and adjusting the settings based on the conducted spectral calibration.

2. The apparatus of claim 1, wherein the user profile information comprises eye optical properties and wherein the at least one memory and the computer program code are configured to, with the at least one processor, cause the apparatus to:

adjust the spectral power distribution of the light source based on the eye optical properties.

3. The apparatus of claim 1, comprising the optical element(s) being configured to collect and to intermix emitted components of the light source to generate dynamic light beam(s) configured for illuminating the one or more regions of the eye.

4. The apparatus of claim 1, wherein the light source comprises a plurality of light transmitters, at least one of the plurality of light transmitters being configured to emit light in one or more of a different spectral band or in different intensity than other ones of the plurality of light transmitters.

5. The apparatus of claim 4, wherein the at least one memory and the computer program code are configured to, with the at least one processor, cause the apparatus to:

adjust spectral power distribution of at least two light transmitters based on the user profile information.

6. The apparatus of claim 5, wherein at least one of the light transmitters is configured to emit light with one or more of a wavelength between 900-2600 nm or with an adjustable intensity.

7. The apparatus of claim 1, comprising a communication interface for transceiving information over a network.

8. The apparatus of claim 1, wherein the optical element(s) comprise at least one of the following: an optical lens, optical fibers, waveguide, and homogenizing rod configured to collect and to intermix emitted components of the light source what consequently generates dynamic light beams configured for illuminating the one or more regions of the eye.

9. The apparatus of claim 1, wherein the apparatus is exchangeably attached as an input device to a second apparatus, the second apparatus being a see-through or near-to-eye optical device.

10. The apparatus of claim 9, wherein the apparatus is attached adjacent to an ocular of the see-through or the near-to-eye optical device so that visible light coming through the ocular is configured to be transmitted to the one or more regions of the eye without being disturbed by the apparatus.

11. The apparatus of claim 10, further comprising a reference element configured to reflect back light emitted from the light source to provide reflected reference data to the sensor, wherein the reference element is arranged so that the visible light coming through the ocular is configured to be transmitted to the one or more regions of the eye without being disturbed by the reference element.

12. The apparatus of claim 1, wherein the at least one memory and the computer program code are configured to, with the at least one processor, cause the apparatus to:

receive settings, from a cloud server, comprising at least one or more of the following:

user profile information containing optical properties of the one or more regions of the eye of the user;

latest updated spectral power distribution (SPD) settings to maximize contrast between one or more of selected features, or data from spectral calibration; or environmental information of the apparatus; and adjust the illuminating light based on the settings.

13. The apparatus of claim 1, comprising a user wearable apparatus, wherein the at least one memory and the computer program code are configured to, with the at least one processor, cause the apparatus to:

transmit the gaze direction information to a second apparatus as input data.

14. The apparatus of claim 1, wherein the at least one memory and the computer program code are configured to, with the at least one processor, cause the apparatus to:

capture eye's optical characteristics data of a user;

transmit the eye's optical characteristics data to a cloud server for identification;

receive settings from a cloud server, comprising user profile information in response to determining identification by the cloud server; and adjust the illuminating light based on the settings.

15. The apparatus of claim 1, wherein the at least one memory and the computer program code are configured to, with the at least one processor, cause the apparatus to:

capture eye's optical characteristics data of a user;

adjust the illuminating light to produce a dynamic light beam;

update the user profile information based on the dynamic light beam associated with the eye's optical characteristics data;

determine environmental information of the apparatus;

transmit updated settings to a cloud server, comprising at least one of the following:

user profile information containing optical properties of the one or more regions of the eye of the user;

latest updated spectral power distribution (SPD) settings to maximize contrast between one or more of selected features; or data from spectral calibration; and environmental information of the apparatus.

16. A method for determining gaze direction information in an apparatus comprising a light source configured for forming illuminating light to one or more regions of an eye of a user, optical element(s) configured to guide the illuminating light from the light source to the one or more regions of the eye, wherein the illuminating light is dynamically adjustable and configured to generate a dynamic light beam on the one or more regions of the eye, and a sensor configured to capture reflected light from the one or more regions of the eye and generate reflection eye data, the method comprising:

maintaining settings comprising user profile information;
 adjusting spectral power distribution of the light source based on the user profile information;
 receiving the reflection eye data; and
 generating the gaze direction information based on the reflection eye data, and conducting spectral calibration of the apparatus by performing at least the following steps:
  scanning the one or more regions of the eye through different spectral bands, or combinations of spectral bands, of the light source and capturing an image by the sensor for each different spectral band;
  comparing image attribute(s) of at least two captured images;
  selecting at least one image based on the comparison;
  one or more of defining an attribute value or creating an index list based on the significance of the selected image;
  determining an intensity of at least one spectral band using one or more of the attribute value or index list; and
  adjusting the settings based on the conducted spectral calibration.

17. The method of claim 16, comprising collecting and intermixing emitted components of the light source to generate dynamic light beam(s) illuminating the one or more regions of the eye.

\* \* \* \* \*